US012778558B2

(12) United States Patent
Zhou et al.

(10) Patent No.: US 12,778,558 B2
(45) Date of Patent: Nov. 3, 2026

(54) ENHANCEMENT OF LOCAL FEATURES IN ULTRASOUND

(71) Applicant: FUJIFILM SONOSITE, INC., Bothell, WA (US)

(72) Inventors: Yong Zhou, Woodinville, WA (US); Bo Zhuang, Redmond, WA (US); Jean Tsou, Seattle, WA (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 0 days.

(21) Appl. No.: 18/437,131

(22) Filed: Feb. 8, 2024

(65) Prior Publication Data

US 2025/0255584 A1 Aug. 14, 2025

(51) Int. Cl.
*A61B 8/00* (2006.01)
*G06T 5/20* (2006.01)

(52) U.S. Cl.
CPC ............ *A61B 8/5269* (2013.01); *A61B 8/463* (2013.01); *A61B 8/469* (2013.01); *A61B 8/54* (2013.01); *G06T 5/20* (2013.01); *G06T 2207/10132* (2013.01); *G06T 2207/30004* (2013.01)

(58) Field of Classification Search
CPC ....... A61B 8/5269; A61B 8/463; A61B 8/469; A61B 8/54; G06T 5/20; G06T 2207/10132; G06T 2207/30004
See application file for complete search history.

(56) References Cited

U.S. PATENT DOCUMENTS

| | | | | | |
|---|---|---|---|---|---|
| 5,897,503 | A * | 4/1999 | Lyon | A61B 8/00 | 600/459 |
| 8,038,619 | B2 * | 10/2011 | Steinbacher | A61B 8/467 | 600/459 |
| 11,564,861 | B1 * | 1/2023 | Gaines | A61H 23/04 | |
| 2004/0015080 | A1 * | 1/2004 | Kelly | A61B 8/406 | 600/459 |
| 2007/0122021 | A1 * | 5/2007 | Zingaretti | G06T 7/0014 | 382/132 |
| 2008/0247618 | A1 * | 10/2008 | Laine | G06T 7/0012 | 382/128 |
| 2009/0012401 | A1 * | 1/2009 | Steinbacher | A61B 8/467 | 600/459 |
| 2010/0249598 | A1 * | 9/2010 | Smith | A61B 8/4455 | 600/459 |
| 2010/0324423 | A1 * | 12/2010 | El-Aklouk | A61B 8/4488 | 600/444 |

(Continued)

*Primary Examiner* — Sanjay Cattungal
(74) *Attorney, Agent, or Firm* — Womble Bond Dickinson (US) LLP

(57) ABSTRACT

Methods and apparatuses for enhancing local features in ultrasound images are disclosed. In some embodiments, an ultrasound system includes an ultrasound scanner configured to transmit ultrasound at a patient anatomy and receive reflections of the ultrasound from the patient anatomy and a processor. The processor is configured to: generate an ultrasound image based on the reflections and system parameters of the ultrasound system; determine a region of interest (ROI) in the ultrasound image; determine an enhancement property for the ROI; adjust at least one of the system parameters; and generate, based on the at least one of the system parameters being adjusted, a ROI image having the enhancement property enhanced compared to the ROI in the ultrasound image. The ultrasound system also includes a display device configured to simultaneously display the ultrasound image and the ROI image.

22 Claims, 22 Drawing Sheets

(56) References Cited

U.S. PATENT DOCUMENTS

| | | | | |
|---|---|---|---|---|
| 2011/0074244 | A1* | 3/2011 | Osawa | B06B 1/0622 310/318 |
| 2011/0082369 | A1* | 4/2011 | Mohr | A61B 1/043 600/431 |
| 2011/0087107 | A1* | 4/2011 | Lindekugel | A61B 8/4455 600/459 |
| 2011/0313293 | A1* | 12/2011 | Lindekugel | A61B 10/00 600/459 |
| 2012/0165679 | A1* | 6/2012 | Orome | A61B 5/150748 600/461 |
| 2012/0179044 | A1* | 7/2012 | Chiang | A61B 8/14 600/467 |
| 2012/0289836 | A1* | 11/2012 | Ukimura | A61B 8/14 600/463 |
| 2013/0338503 | A1* | 12/2013 | Cohen | A61B 8/4411 600/443 |
| 2013/0338508 | A1* | 12/2013 | Nakamura | A61B 8/4494 600/459 |
| 2014/0031694 | A1* | 1/2014 | Solek | A61B 8/4427 600/459 |
| 2014/0066779 | A1* | 3/2014 | Nakanishi | A61B 8/4444 600/459 |
| 2014/0180116 | A1* | 6/2014 | Lindekugel | A61B 8/4455 600/459 |
| 2014/0276069 | A1* | 9/2014 | Amble | A61B 8/4488 600/447 |
| 2015/0359520 | A1* | 12/2015 | Shan | A61B 8/0858 600/443 |
| 2016/0026894 | A1* | 1/2016 | Nagase | A61B 8/4263 600/443 |
| 2017/0328751 | A1* | 11/2017 | Lemke | G01H 9/00 |
| 2020/0163654 | A1* | 5/2020 | Satir | A61B 8/58 |
| 2021/0059639 | A1* | 3/2021 | Howell | A61B 8/4444 |
| 2021/0212668 | A1* | 7/2021 | Li | G01S 17/66 |
| 2022/0071593 | A1* | 3/2022 | Tran | A61B 8/463 |

* cited by examiner

1600D

ENHANCEMENT OF LOCAL FEATURES IN ULTRASOUND

FIELD OF THE INVENTION

Embodiments disclosed herein relate to ultrasound systems. More specifically, embodiments disclosed herein are related to enhancing local features in ultrasound images.

BACKGROUND

Ultrasound imaging is a widely-used, non-ionizing diagnostic tool. A high-quality ultrasound image can provide accurate patient information so that the clinicians can make an accurate diagnosis. System settings of conventional ultrasound systems usually balance the entire image and consider the patient variety. Imaging of the actual region of interest (ROI), such as, for example, a particular nerve for anesthesia or a vessel for vascular access, still has room to improve. For instance, complaints from clinicians in terms of insufficient resolution, penetration, or contrast are common. In addition, different clinicians may have different preferences, and different patients may require different settings as well. All these lead to more requests for more optimized images, especially on the ROI. Because in clinical practice, the clinicians don't use all the information in the image, a big portion of the image actually contains unnecessary information, which leads to a waste of system acquisition and computation power.

The issues surrounding ROIs and the waste of resources are difficult to solve for at least the following reasons. First, the patient's variety and clinician's preferences can vary substantially and impede having one or even several general settings that satisfy all the clinical use cases. Second, the initial settings try to balance the entire images, which makes the imaging of each individual ROI sub-optimal. Third, it is hard to achieve imaging stability and acceptable imaging qualities due to the big patient varieties and even the anatomy varieties within the same patient.

SUMMARY

Methods and apparatuses for enhancing local features in ultrasound images are disclosed. In some embodiments, an ultrasound system includes an ultrasound scanner configured to transmit ultrasound at a patient anatomy and receive reflections of the ultrasound from the patient anatomy and a processor. The processor is configured to: generate an ultrasound image based on the reflections and system parameters of the ultrasound system; determine a region of interest (ROI) in the ultrasound image; determine an enhancement property for the ROI; adjust at least one of the system parameters; and generate, based on the at least one of the system parameters being adjusted, a ROI image having the enhancement property enhanced compared to the ROI in the ultrasound image. The ultrasound system also includes a display device configured to simultaneously display the ultrasound image and the ROI image.

In some other embodiments, an ultrasound system includes an ultrasound scanner configured to transmit ultrasound at a patient anatomy and receive reflections of the ultrasound from the patient anatomy as part of a current ultrasound examination. The ultrasound system also includes a processor system. The processor system is configured to generate an ultrasound image based on the reflections and system parameters of the ultrasound system, and determine a region of interest (ROI) in the ultrasound image.

The processor system is also configured to determine an enhancement property for the ROI, determine, based on the enhancement property, ROI image properties for the ROI in the ultrasound image, and determine adjustments to one or more of the system parameters, the adjustments corresponding to the ROI image properties. The processor system is also configured to generate, based on the adjustments, ROI images having the enhancement property enhanced compared to the ROI in the ultrasound image, the ROI images excluding image content of the ultrasound image that is not contained in the ROI. The ultrasound system also includes a display device configured to simultaneously display the ultrasound image and the ROI images.

In yet some other embodiments, the ultrasound system includes an ultrasound scanner configured to transmit ultrasound at a patient anatomy and receive reflections of the ultrasound from the patient anatomy as part of a current ultrasound examination. The ultrasound system also includes a memory storage device configured to store system parameters, determined as part of a previous ultrasound examination, to enhance an enhancement property in a region of interest (ROI) in a previous ultrasound image generated during the previous ultrasound examination. The ultrasound system also includes a processor system configured to, as part of the current ultrasound examination, generate an ultrasound image based on the reflections, determine a current ROI in the ultrasound image, the current ROI including the patient anatomy, determine that the ROI and the current ROI include the patient anatomy, configure, based on the determination that the ROI and the current ROI include the patient anatomy, the ultrasound system with the system parameters stored in the memory storage device, and generate, based on the ultrasound system configured with the system parameters, a ROI image having the enhancement property enhanced compared to the current ROI in the ultrasound image. The ultrasound system further includes a display device configured to simultaneously display the ultrasound image and the ROI image.

BRIEF DESCRIPTION OF THE DRAWINGS

The appended drawings illustrate examples and are, therefore, exemplary embodiments and not considering to be limiting in scope.

DETAILED DESCRIPTION

Figure 1A:
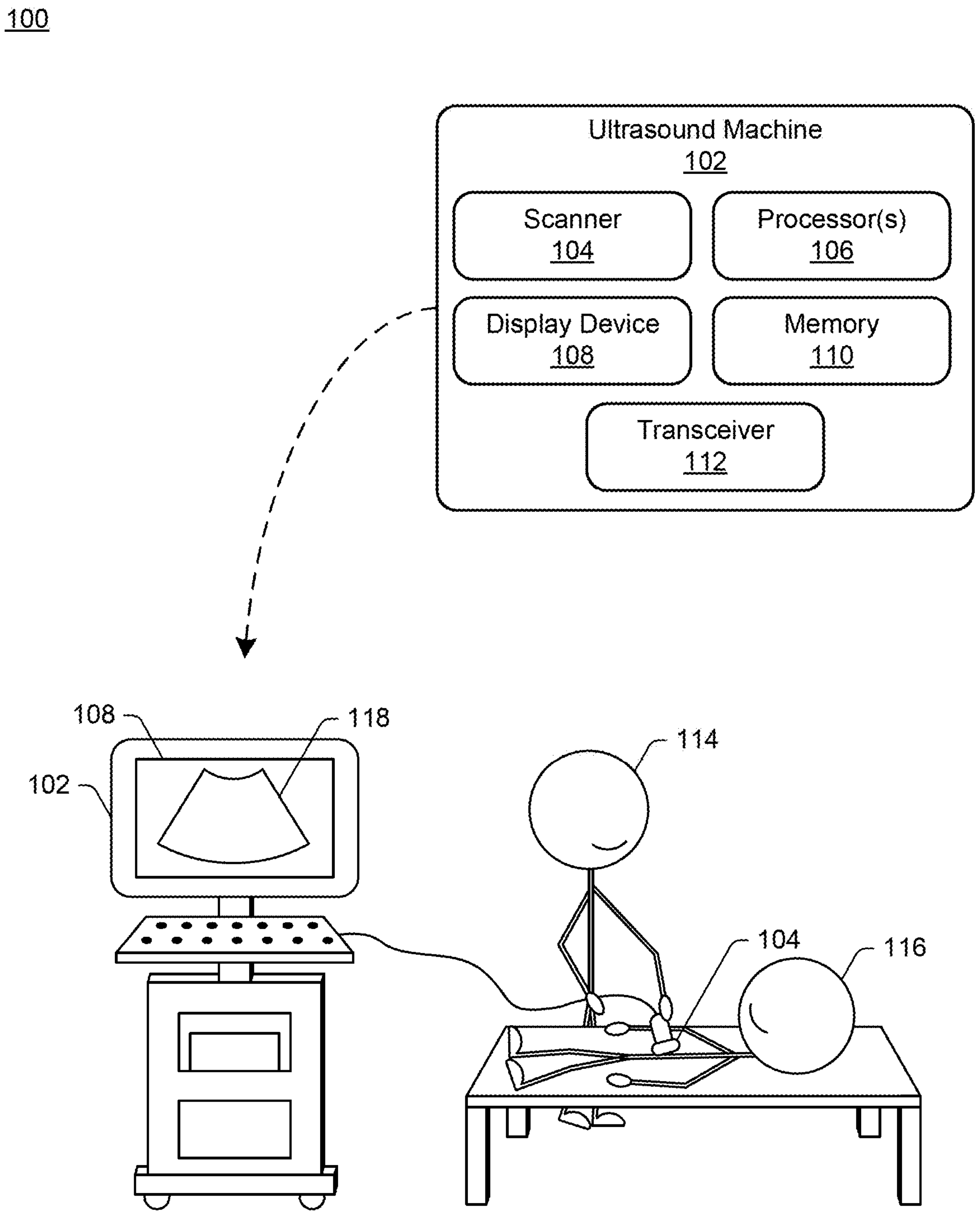
FIG. 1A illustrates an ultrasound system in an environment for enhancing local features in ultrasound.

In the following description, numerous details are set forth to provide a more thorough explanation of the present invention. It will be apparent, however, to one skilled in the art, that the present invention may be practiced without these specific details. In other instances, well-known structures and devices are shown in block diagram form, rather than in detail, in order to avoid obscuring the present invention.

Systems, devices, and techniques are disclosed herein for enhancing ultrasound images by adjusting system parameters and generating an ultrasound image with a property that has been enhanced. In some embodiments, the enhancement is applied to a region of interest (ROI) in an ultrasound image. The ultrasound system can determine an enhancement property for the ROI and then adjust one or more system parameters to enable the ultrasound system to generate a ROI image having a property enhanced compared to the original, or previous, ROI in the ultrasound image. In this manner, local feature enhancement can enhance an arbitrary property of an ROI image.

Term Examples

The terms "connect," "connected," "contact" "coupled" and/or the like are broadly defined herein to encompass a variety of divergent arrangements and assembly techniques. These arrangements and techniques include, but are not limited to (1) the direct joining of one component and another component with no intervening components therebetween (i.e., the components are in direct physical contact); and (2) the joining of one component and another component with one or more components therebetween, provided that the one component being "connected to" or "contacting" or "coupled to" the other component is somehow in operative communication (e.g., electrically, fluidly, physically, optically, etc.) with the other component (notwithstanding the presence of one or more additional components therebetween). It is to be understood that some components that are in direct physical contact with one another may or may not be in electrical contact and/or fluid contact with one another. Moreover, two components that are electrically connected, electrically coupled, optically connected, optically coupled, fluidly connected or fluidly coupled may or may not be in direct physical contact, and one or more other components may be positioned therebetween.

As used herein, the terms "including" and "comprising" mean the same thing.

As used herein, the term "transmit aperture" or "TX aperture" is defined as the multiplication of a number of elements used for transmitting and the pitch between elements, and the term "receive aperture" is defined as multiplication of a number of elements used for receiving and the pitch between elements.

As used herein, the term "transmit sequence" refers to the multiple transmit (Tx) transmissions and receive accordingly to form a final ultrasound image. In some embodiments, the transmit sequence includes information indicating the width of the Tx beam for each Tx transmission and/or the order (e.g., left to right, right to left, etc.). Other information can be included in the transmit sequence.

As used herein, the term "multi-line method" refers to increasing the frame rate when performing ultrasound imaging, by transmitting a broad beam and then receiving, or acquiring, several lines under the one broad beam, where the several lines are used to form the final ultrasound image. Thus, in some embodiments, several beams are received from a single transmit (Tx) beam. Note that different methods to implement the multi-line method are well-known in the art.

As used herein, the term "persistence" is defined as the temporal average between frames. In some embodiments, persistence is the temporal averaging that takes a weighted average between successive image frames to reduce the ultrasound noise (e.g., speckle noise, etc.).

As used herein, the term "flow strength" is the color flow signal strength that indicates the strength of the blood flow in a patient. In some embodiments, the flow strength can be fast but weak, slow but strong, or other combinations.

As used herein, the term "flow continuity" is how smooth the blood flow is (e.g., continuous showing up or sometimes down, etc.). In some embodiments, flow continuity is defined using a flow continuity equation that states that the volume of blood flowing into a chamber is equal to the volume flowing out of the same chamber.

As used herein, the term "flow dynamic range" is the difference between the maximum and minimum blood flow.

As used herein, the term "color map" is a color representation. The color map can be used for color flow mapping in ultrasound color flow doppler. In color doppler, in some embodiments, the color varies in proportion to the flow velocity. In some embodiments, the color representation is assigned to the flow velocity, such as, for example, hot or RGB, thereby displaying flow velocity at each site.

As used herein, the term "spatial smooth filtering" is the spatial filtering used to smooth out the color image.

As used herein, the term "color mask" is the mask to differentiate the color and B-mode image.

An Example Ultrasound System

FIG. 1A illustrates some embodiments of an ultrasound system in an environment 100 for enhancing local features in ultrasound. The ultrasound system includes an ultrasound machine 102 and an ultrasound scanner 104.

The ultrasound machine 102 generates high-frequency sound waves (e.g., ultrasound) and imaging data based on the ultrasound reflecting off a patient anatomy/body structure. The ultrasound machine 102 includes various components, some of which include the scanner 104, one or more processors 106, a display device 108, a memory 110, and a transceiver 112.

A user 114 (e.g., nurse, ultrasound technician, operator, sonographer, clinician, etc.) directs the scanner 104 toward a patient 116 to non-invasively scan internal bodily structures (e.g., patient anatomies such as organs, tissues, bones, etc.) of the patient 116 for testing, diagnostic, therapeutic, or procedural reasons. In some embodiments, the scanner 104 includes an ultrasound transducer array and electronics communicatively coupled to the ultrasound transducer array to transmit ultrasound signals to the patient's anatomy and receive ultrasound signals reflected from the patient's anatomy. In some embodiments, the scanner 104 is an ultrasound scanner, which can also be referred to as an ultrasound probe. The patient 116 can be a person, as is illustrated in FIG. 1A, or an animal. Hence, the techniques disclosed herein can be practiced in various settings, including clinical or pre-clinical settings.

The display device 108 is coupled to the processor 106, which can include any suitable processor, number of processors, or processor system, such as one or more CPUs, GPUs, vector processors, RISC processors, CISC processors, VLIW processors, etc. The processor 106 can execute instructions stored on memory 110 to perform operations disclosed herein for enhancing local features in ultrasound. For example, the processor 106 can process the reflected ultrasound signals to generate ultrasound data, including an ultrasound image. The display device 108 is configured to generate and display an ultrasound image (e.g., ultrasound image 118) of the anatomy based on the ultrasound data generated by the processor 106 from the reflected ultrasound signals detected by the scanner 104. In some aspects, the ultrasound data includes the ultrasound image 118 or data representing the ultrasound image 118.

Capturing ultrasound data from a subject using a transducer assembly generally includes generating ultrasound signals, transmitting ultrasound signals into the subject, and receiving ultrasound signals reflected by the subject. A wide range of frequencies of ultrasound can be used to capture ultrasound data, such as, for example, low-frequency ultrasound (e.g., less than 15 Megahertz (MHz)) and/or high-frequency ultrasound (e.g., greater than or equal to 15 MHz). A particular frequency range to use can readily be determined based on various factors, including, for example, depth of imaging, desired resolution, and so forth.

In some embodiments, the system electronics include one or more processors (e.g., the processor(s) 106 from FIG. 1), integrated circuits, application-specific integrated circuits (ASICs), Field Programmable Gate Arrays (FPGAs), and power sources to support functioning of the ultrasound machine 102. In some embodiments, the ultrasound machine 102 also includes an ultrasound control subsystem having one or more processors. At least one processor, FPGA, or ASIC can cause electrical signals to be transmitted to the transducer(s) of the scanner 104 to emit sound waves and also receives electrical pulses from the scanner 104 that were created from the returning echoes. One or more processors, FPGAs, or ASICs can process the raw data associated with the received electrical pulses and form an image that is sent to an ultrasound imaging subsystem, which causes the image (e.g., the image 118 in FIG. 1) to be displayed via the display device 108. Thus, the display device 108 displays ultrasound images from the ultrasound data processed by the processor(s) of the ultrasound control subsystem.

In some embodiments, the ultrasound machine 102 also includes one or more user input devices (e.g., a keyboard, a cursor control device, a microphone, a camera, touchscreen, etc.) that input data and enable taking measurements from the display device 108 of the ultrasound machine 102. The ultrasound machine 102 can also include a disk storage device (e.g., computer-readable storage media such as read-only memory (ROM), a Flash memory, a dynamic random-access memory (DRAM), a NOR memory, a static random-access memory (SRAM), a NAND memory, and so on) for storing the acquired ultrasound data. In some embodiments, the disk storage device includes the memory 110, which is local to the ultrasound machine 102. Alternatively, the memory 110 used for storing the acquisition data can be remote, such as on a remote server communicatively connected to the ultrasound machine 102. In addition, the ultrasound machine 102 can include a printer that prints the image from the displayed data.

Example Workflows

Figure 1B:
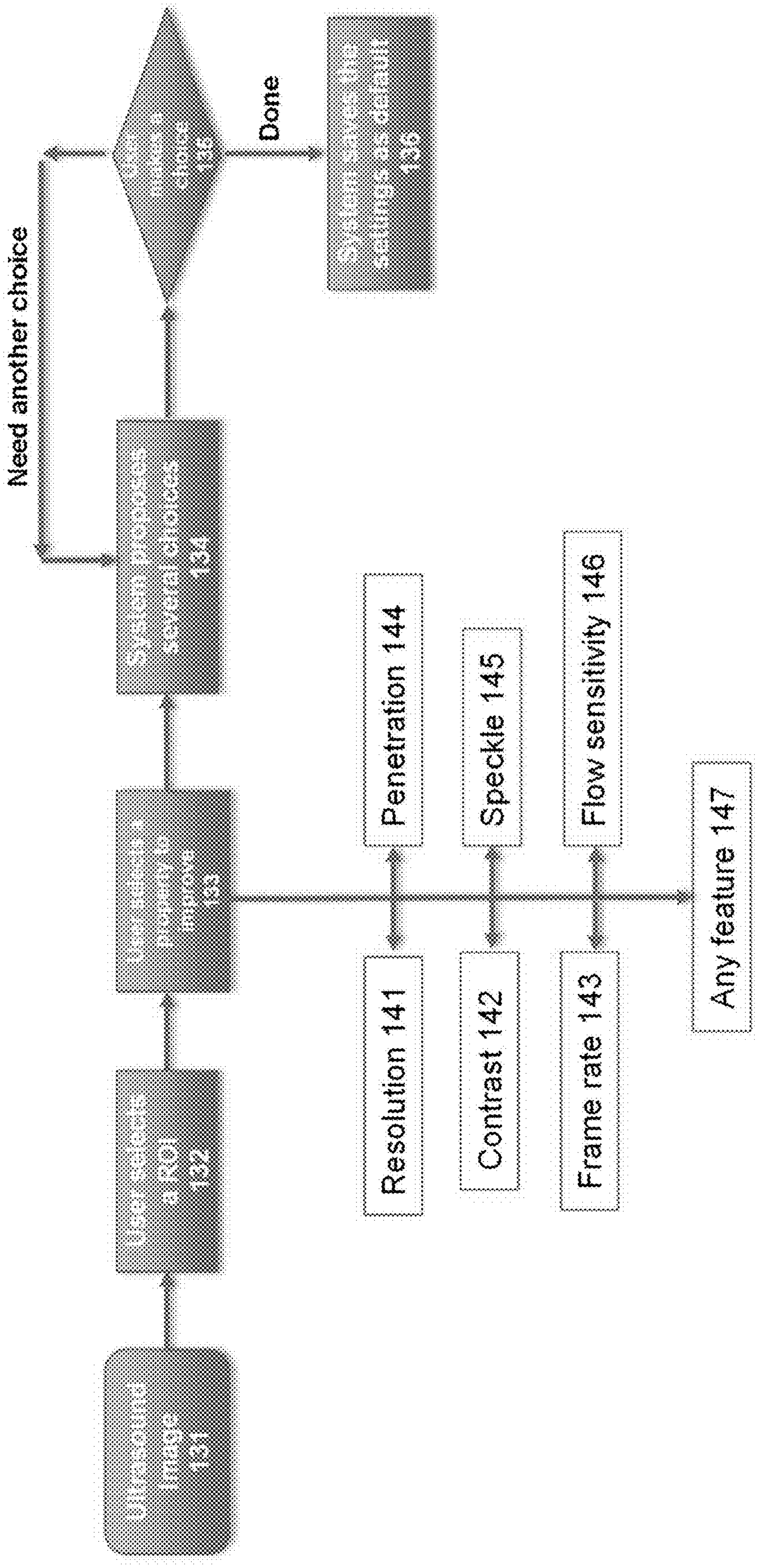
FIG. 1B illustrates some embodiments of enhancement of local feature workflow.

FIG. 1B illustrates some embodiments a local feature workflow for performing an enhancement (e.g., an arbitrary enhancement of features) of an ROI. Referring to FIG. 1B, the workflow begins with an ultrasound image (131), and a user can select a ROI (132) in the ultrasound image (131) where the improvement is needed. Additionally or alternatively, the ROI can be determined by a machine-learned model, such as a neural network, that has been trained to identify a particular patient anatomy, such as an organ, and segment the anatomy as part of the ROI. The user may also select a property for improvement (133), such as resolution (141) including flow resolution, penetration (144), contrast (142), speckle reduction (145), flow sensitivity (146), and frame rate (143), which the ultrasound system receives. Once the ultrasound system receives the request, e.g., from the user, the ultrasound system generates several choices with the enhanced property (134) from which the user can choose (135). If the user selects one of the choices, the ultrasound system saves the setting corresponding to the selected choice as a new default (136). In other words, users are able to determine for themselves which of the enhanced ROIs meets their needs (e.g., satisfies their individual needs or requirements for performing the examination). If the user does not like the choices provided and/or needs to make another choice, the ultrasound system loops back and generates several new choices (134) from which the user may choose until the user is happy with the setting.

The properties listed here, including resolution (141) (e.g., flow resolution), penetration (144), contrast (142), speckle reduction (145), flow sensitivity (146), frame rate (143), are provided as examples and generally the properties can include any feature (147). Any other additional properties can be improved as well, e.g., based on the users letting the system know which property they want to enhance. Here for simplicity, the above properties are used as examples to describe the techniques disclosed herein, which are listed below. The example properties disclosed herein are exemplary and not intended to be limiting.

Method and Workflow for Resolution Enhancement

Figure 2:
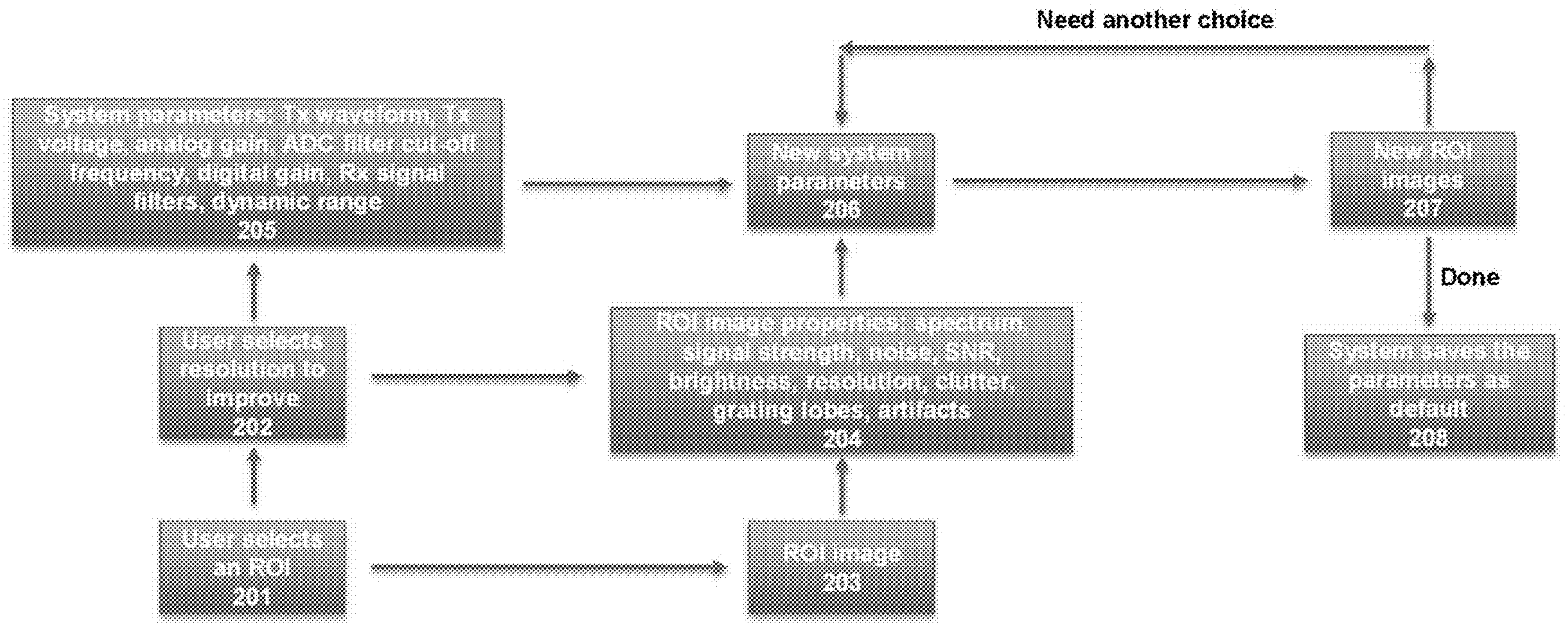
FIG. 2 illustrates some embodiments of a method and workflow for resolution enhancement.

FIG. 2 illustrates some embodiments of a method and workflow for resolution enhancement. Referring to FIG. 2, the user selects an ROI from an ultrasound image (201) and selects resolution as the property to be enhanced (202). Although here and in other figures the ROI is user selected, in some embodiments, the system determines an ROI automatically and without user intervention. For instance, the system can use a machine-learned model to identify a patient anatomy in an image and select the ROI so that includes the determined anatomy. The system can determine the anatomy based solely on the image itself, or in some cases, also based on additional information, such as, for example, an examination type (e.g., a preset), a protocol (or step of a protocol), patient history data, a previous ultrasound examination, etc.

As shown in FIG. 2, for resolution enhancement, certain ROI image properties are extracted from the ROI image. In addition, certain system parameters are analyzed against the ROI image properties and then subsequently updated to generate new sets of ROI images. For clarity, the resolution here means spatial resolution, including lateral resolution and/or axial resolution. In some embodiments, approximated by −6 dB full-width half-maximum (FWHM) beam profile, the lateral resolution is defined as:

$$LR = 0.4 \times \lambda \times F/A, \quad \text{Eq. (1)}$$

where λ is ultrasound wavelength, which is inverse proportional to center frequency, F is the focal distance, and A is the active aperture. Because ultrasound imaging is a two-way imaging modality, the final lateral resolution of the image is determined by both transmit and receive:

$$LR_{final} = LR_{Tx} \otimes LR_{Rx}, \quad \text{Eq. (2)}$$

where $LR_{final}$ is the final image lateral resolution, $LR_{Tx}$ is the transmit lateral resolution, and $LR_{Rx}$ is the receive lateral resolution. From Eqs. (1) and (2), the lateral resolution is mainly determined by transmit waveform frequency, transmit aperture, transmit focal distance, receive signal frequency, receive aperture, and receive focal distance. Because in ultrasound imaging, usually dynamic focusing is applied for receiving, the receive focal distance has little or no impact on the final image lateral resolution. From the system receiving signal path side, the receive signal frequency is largely based on receive signal filters. Because lateral resolution is defined as −6 dB FWHM, the corresponding signal strength is important as well and plays a role in determining the lateral resolution. In general, the following system parameters can impact the signal strength and thus may impact the lateral resolution: Tx voltage, analog gain, ADC filter cut-off frequency, digital gain, and dynamic range. Further, the noise and artifacts (such as grating lobes, clutters, etc.) should be low enough so that they won't impact the true signal strength for lateral resolution estimation.

Similar to the definition of lateral resolution, in some embodiments, the axial resolution is defined as −6 dB FWHM beam profile along axial direction, which can be expressed as:

$$AR = 0.77 \times c/B, \quad \text{Eq. (3)}$$

where c is speed of sound in medium, which is a constant for the medium, and B is the final received signal bandwidth. Again, because ultrasound imaging is a two-way imaging modality, the final axial resolution of the image can be determined by both transmit and receive axial resolutions:

$$AR_{final} = AR_{Tx} \otimes AR_{Rx}, \quad \text{Eq. (4)}$$

where $AR_{final}$ is the final image axial resolution, $AR_{Tx}$ is the transmit axial resolution, and $AR_{Rx}$ is the receive axial resolution. From Eqs. (3) and (4), the axial resolution is mainly determined by transmit waveform bandwidth and receive signal bandwidth. Similar to the lateral resolution case, the signal strength, noise, and artifact level can impact the final axial resolution. Therefore, when enhancing the axial resolution is desired, these parameters and properties of the ROI image can be determined.

After the users select a ROI (201) to enhance the resolution (202), the ultrasound system determines the corresponding parameters mentioned above (205), including Tx waveform, Tx voltage, analog gain, ADC filter cut-off frequency, digital gain, Rx signal filters, and dynamic range, e.g., by identifying values and memory addresses for these parameters. Further, the ultrasound system analyzes the ROI image 203 to determine the corresponding properties mentioned above (204), including spectrum, signal strength, noise, SNR, brightness, resolution, clutter, grating lobes and artifacts. Then, the ultrasound system updates the system parameters based on the ROI image properties to create new system parameters (206). For example, if the ultrasound system determines that the ROI image center frequency is lower than the Tx waveform and the ROI image signal to noise ratio (SNR) is still very good (e.g., bigger than 10 dB), the ultrasound system can increase the center frequency of the receive signal filters to increase lateral resolution. On the other hand, if the ROI image SNR is low, the ultrasound system can first increase analog gain and then change the Tx waveform to a higher frequency to increase lateral resolution. In some embodiments, the lateral and axial resolutions are combined in the same workflow for simplicity. Alternatively, the lateral and axial resolutions can be separated in different workflows. Therefore, in some embodiments, in the ROI image, the spectrum is used to represent both image center frequency and bandwidth; in system parameters, the Tx waveform is used to represent both the Tx center frequency and bandwidth.

Using the new parameters, the ultrasound system generates new ROI images (207). If the user likes a new ROI image and makes a choice to select the setting used to generate this new ROI image, then the ultrasound system saves the setting as a new default (208). If the user needs to make another choice, the ultrasound system loops back and generates several new choices (206) from which the user may choose until the user is happy with the setting.

Method and Workflow for Penetration Enhancement

Figure 3:
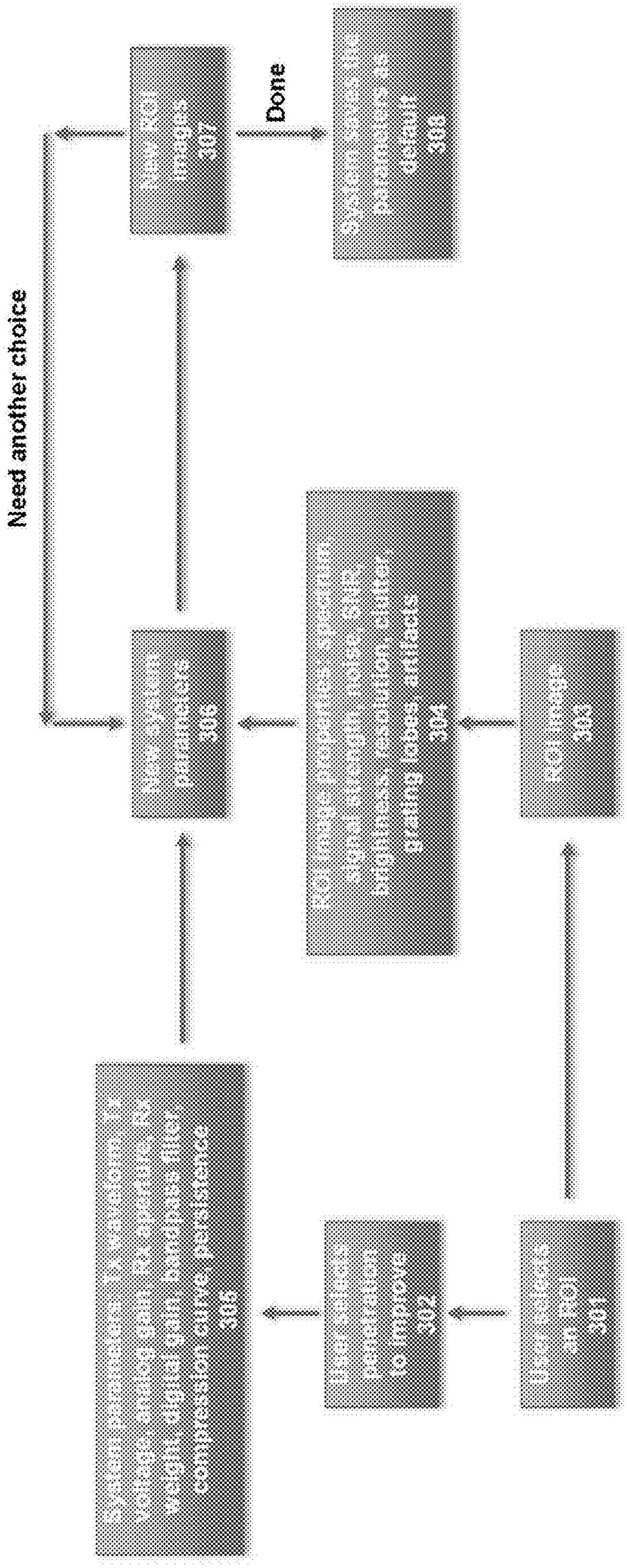
FIG. 3 illustrates some embodiments of a method and workflow for penetration enhancement.

FIG. 3 illustrates some embodiments of a method and workflow for penetration enhancement. Referring to FIG. 3, the user selects an ROI from an ultrasound image (301) and selects ROI image penetration as the property to be enhanced (302).

Different from resolution enhancement discussed previously with respect to FIG. 2, to increase ROI image penetration with respect to FIG. 3, the signal strength, noise level, and artifacts can play more significant roles. In some embodiments, if the users want to enhance penetration in the ROI, then the resolution of the ROI image is manipulated. In ultrasound imaging, the round-trip signal S(f) can be expressed as:

$$S(f) = (k \times T(f) \times P(f) \times O(f) \times P(f) \times R(f) + N(f) + A(f)) \times G(f) \times F(f), \quad \text{Eq. (5)}$$

where k is a constant coefficient, T(f) is the transmit function, P(f) is the one-way propagation function, O(f) is the object function, R(f) is the receive function, N(f) is the noise, A(f) is the artifact (which is minimal in most cases and can be neglected), G(f) is the gain function, and F(f) is the filter function in the system. In some embodiments, the T(f) includes the transmit waveform, transmit voltage, and transducer transmit impulse response. P(f) is usually dependent on the actual human tissue type. The higher the frequency f, the higher the attenuation of the signals. In an example, R(f) only includes the transducer receive impulse response and does not include other receive signal and image process functions. In an example, G(f) includes all the analog and digital gains. In an example, F(f) includes all the system signal filter functions. As shown in Eq. (5), in some embodiments, one way to increase the signal strength without increasing the noise is to increase the strength of the transmit function T(f), to reduce attenuation due to the propagation function P(f), and to increase the receive function R(f). In some other embodiments, the transmit function T(f) is limited by safety regulations (such as thermal and mechanical safety regulations) and is maximized within the safety regulations. The propagation function P(f) and receive function R(f) are fixed for a given application and a given transducer. One method to increase the signal strength is to take advantage of lower attenuation from lower frequency signals. However, the image resolution can decrease because of the lower frequency signals. Therefore, if the ROI image already has good resolution, the system can decrease the Tx waveform frequency to increase the signal strength and thus the penetration.

In addition, because the N(f) has a different spectrum than desired signals, one way to increase the signal strength is to increase the gain G(f) and adjust the filter F(f) to pass only the signal band. Thus, the system can take the ROI image data and determine the actual signal spectrum. For example, if the gain G(f) and F(f) don't align with the actual ROI image spectrum, one way to increase the signal strength (a.k.a. penetration) is to adjust the G(f) and F(f) to be more spectrally consistent with the actual ROI image.

Further, because the penetration in this case is the perception of the image on the screen by one or more users, the gray scale of the image also impacts the penetration from a user perspective. Therefore, any parameters related to the manner in which the image is displayed on the screen can impact the penetration as well, such as, for example, the compression curve. In some embodiments, the system increases the lower gray brightness to introduce better penetration to the users.

After the user selects a ROI (301) to enhance the penetration (302), the ultrasound system determines (e.g., pulls out from memory) one or more of the corresponding parameters mentioned above (305), including Tx waveform, Tx voltage, analog gain, Rx aperture, Rx weight, digital gain, bandpass filter (e.g., a Quadrature Bandpass Filter (QBP), etc.), compression curve, and persistence. Further, the ultrasound system analyzes the ROI image (303) to determine the corresponding properties mentioned above (304), including spectrum, signal strength, noise, SNR, brightness, resolution, clutter, grating lobes and artifacts. Then, the ultrasound system updates the system parameters based on the ROI image properties to create new system parameters (306). Using the new parameters, the ultrasound system generates new ROI images (307). If the user likes a new ROI image and makes a choice, the ultrasound system saves the setting corresponding to the selected choice (e.g., a selected ROI image) as a new default (308). If the user needs to make another choice, the ultrasound system loops back and generates several new choices (306) from which the user may choose until the user is happy with the setting.

There are many ways to increase image penetration. However, the improvement in penetration may introduce degradation in resolution or increase in noise level. Therefore, while ROI image data is acquired, the system can update the corresponding parameters accordingly and adaptively, thus continuing to provide acceptable results to the user.

Method and Workflow for Contrast Enhancement

Figure 4:
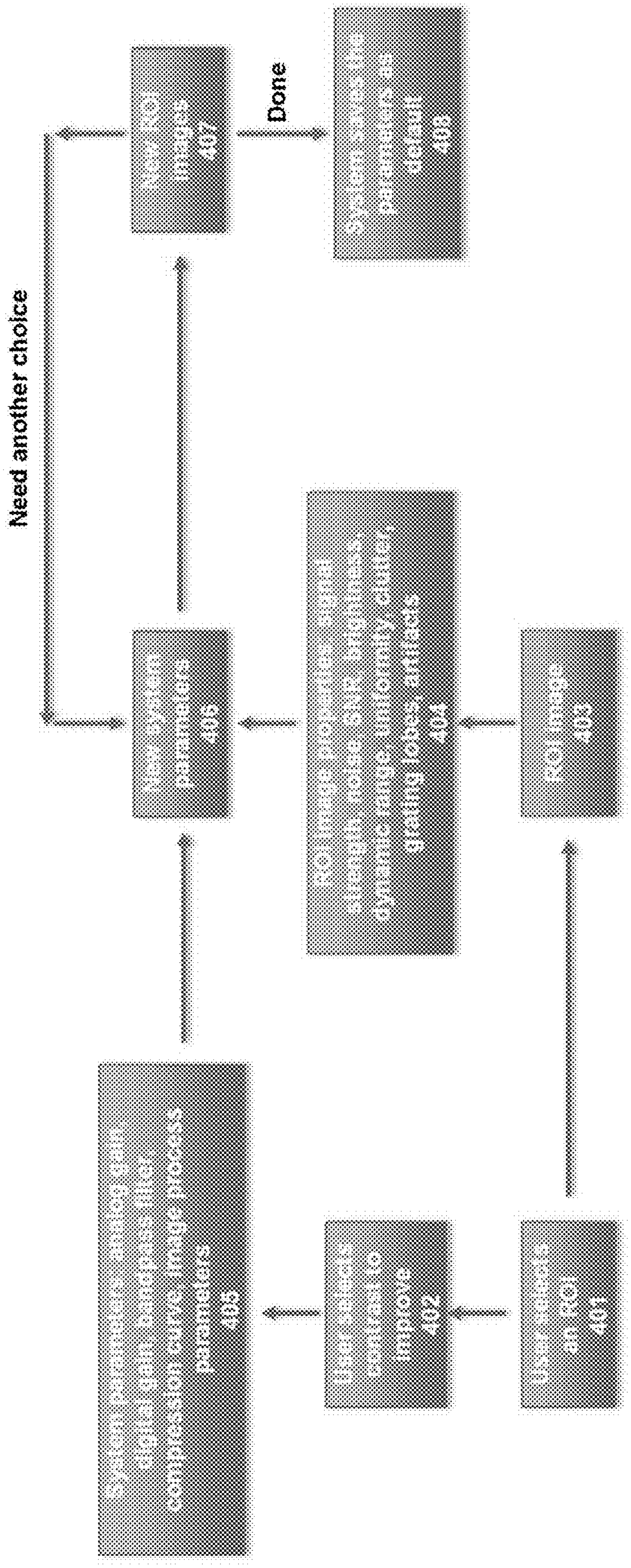
FIG. 4 illustrates some other embodiments of a method and workflow for contrast enhancement.

FIG. 4 illustrates some embodiments of a method and workflow for contrast enhancement. Referring to FIG. 4, the user selects an ROI from an ultrasound image (401) and selects contrast as the property to be enhanced (402).

In some embodiments, the contrast in ultrasound imaging is defined as the signal strength difference between adjacent regions, as shown in Eq. (6):

$$C(AB) = S(A) - S(B), \quad \text{Eq. (6)}$$

where C(AB) is contrast between region A and B, S(A) is the signal strength in region A, and S(B) is the signal strength in region B. Note that region A and region B are dependent on the ROI selected by the users. Another useful parameter to control contrast enhancement is the contrast-to-noise ratio (CNR), which can be expressed as:

$$CNR(AB) = C(AB)/N \quad \text{Eq. (7)}$$

where CNR(AB) is the CNR over regions A and B, and N is the noise. The clinician can maintain the same noise level while increasing the contrast. Otherwise, the contrast over regions A and B may be buried in the noise and become less useful.

As shown in FIG. 4, there are many parameters that can impact the contrast, including gains and filters. Further, the imaging process parameters and the compression curve can play important roles in this context. Because from the user perspective, the contrast is the image contrast presented on the screen instead of the original signal or image contrast, any signal brightness mapping parameters such as, for example, the compression curve and image processing parameters will change the user-perceived contrast. Therefore, to implement a simple contrast change, the system can be controlled to update the compression curve to increase the perceived brightness difference between S(a) an S(B), while keeping the CNR high enough for reasonable image display. Therefore, gain and filter adjustments or even Tx function change can be used to affect contrast. This consideration is similar to the penetration and resolution enhancement discussed above. In some cases, a good signal-to-noise ratio (SNR) is considered by some users to be the starting point for all the other properties, including resolution, penetration, and of course the contrast being discussed herein. However, in some embodiments, this impact is secondary and is not listed in FIG. 4.

After the user selects a ROI (401) to enhance the contrast (402), the ultrasound system determines (e.g., pulls out from memory) the corresponding parameters (405), including one or more of analog gain, digital gain, bandpass filter, compression curve, and image process parameters. The ultrasound system also analyzes the ROI image (403) to determine the corresponding properties (404), including signal strength, noise, SNR, brightness, dynamic range, uniformity, clutter, grating lobes, and artifacts. Then, the ultrasound system updates the system parameters based on the ROI image properties to create new system parameters (406). Using the new parameters, the ultrasound system generates new ROI images (407). If the user likes an ROI image and makes a choice (e.g., selection of an ROI image), the ultrasound system saves the setting (e.g., adjusted parameters) corresponding to the selected choice as a new default (408). If the user needs to make another choice, the ultrasound system loops back and generates several new choices (406) from which the user may choose until the user is happy with the setting.

Method and Workflow for Image Processing Enhancement

Figure 5:
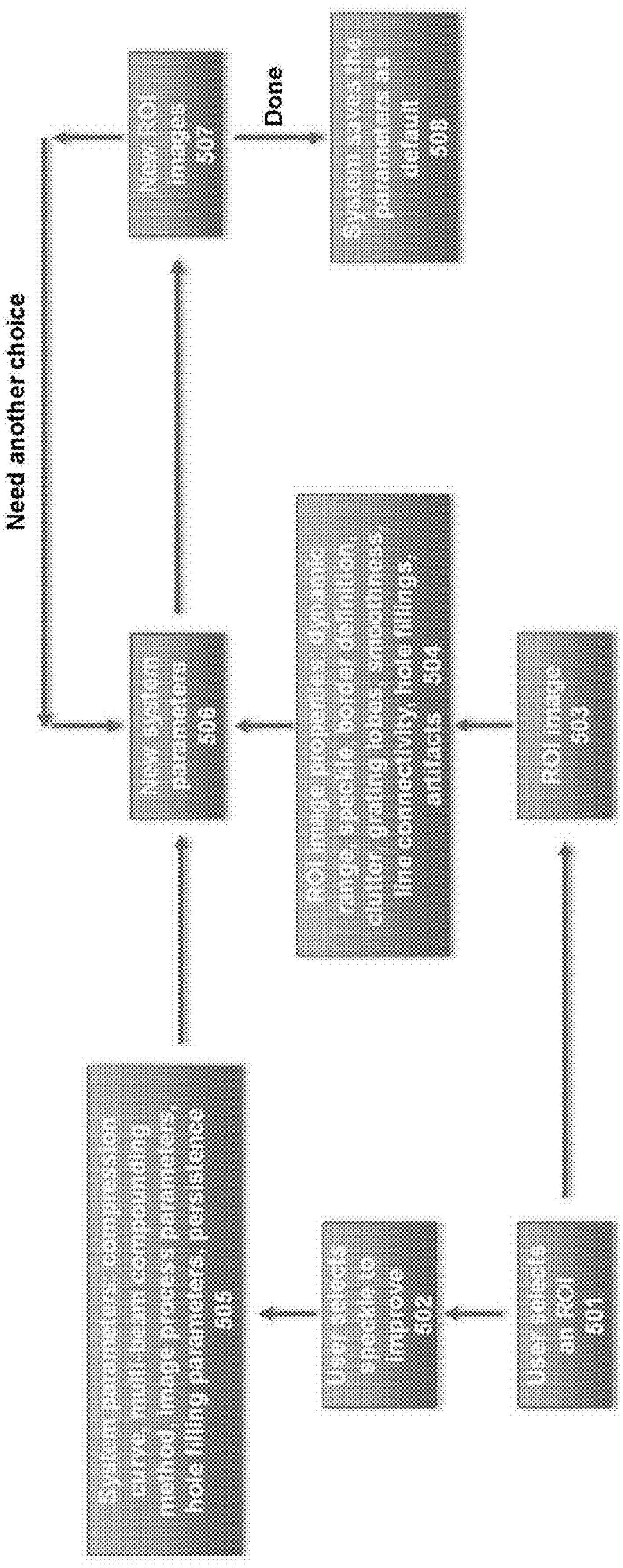
FIG. 5 illustrates yet other embodiments of a method and workflow for image processing enhancement.

FIG. 5 illustrates some embodiments of a method and workflow for image processing (e.g., speckle) enhancement. Referring to FIG. 5, the user selects an ROI from an ultrasound image (501) and selects an image processing category (e.g., speckle) as the property to be enhanced (502).

Image processing includes many different categories, such as, for example, speckle size, line connectivity, border definition, hole fillings, resolution, contrast, etc. There are several ways to enhance the image processing categories. In some embodiments, image processing enhancement is divided into several more individual property enhancement operations that the user is given the control to request. For example, in some embodiments, the system displays another dropdown menu to the users after they select image processing enhancement, including, but not limited to, the above-mentioned detailed properties: speckle size, line connectivity, border definition, hole fillings, resolution, and contrast. This increases the user interaction complexity and enhances the specific properties a user may want to enhance. Second, in some embodiments, the system uses user image processing enhancement to represent some or all the properties the user may want to enhance. In some embodiments, based on the ROI image and/or a specific anatomy the user selects, the system analyzes the image and determines a property that the user wants to enhance. In some embodiments, the system implements a learning process with some prior information. For example, if the user selects a line, then they probably want to enhance the line connectivity. This method can increase the chance that the proposed enhancements by the system are not the ones the users want to achieve. However, because the system proposes several choices to the users, the system can resolve the potential issue. For example, the system can propose several choices, including one with enhanced line connectivity, one with enhanced border definition, and one with resolution. In some embodiments, it is unnecessary for the system to propose choices along the same enhancement direction. In addition, with more images seen by the system and more inputs the system receives from the users, the system becomes more informed and learns the user's desires and choices and improves the quality of the proposed images, not only the property improvement itself, but also the direction of the improvement. In an example, the user does not need to select any property to enhance at all. For instance, a user may only need to select the ROI, and the system will automatically enhance the ROI and generate one or more ROI images.

Referring back to FIG. 5, after the user chooses image processing and/or an image processing category (e.g., speckle) (502) to enhance and after selecting the ROI, the system determines the following properties from the ROI image (503): dynamic range, speckle, border definition, line connectivity, hole fillings, and artifacts (504). In some embodiments, the artifacts include grating lobes, clutters, etc. The system also checks the current related parameters, such as, for example, compression curve, a multi-beam compounding method using multiple beams to form an ultrasound image, image process parameters (e.g., parameters for spatial filtering to smooth the image or sharpen the image, etc.), hole filling parameters (to fill black hole artifacts generated due to beamforming), persistence, and gain settings (505). Based on the ROI image properties, the system determines the corresponding parameters to update and updates the system parameters based on the ROI image properties to create new system parameters (506). Using the new parameters, the ultrasound system generates new ROI images (507). If the user likes and makes a choice, the ultrasound system saves the setting as a new default (508). If the user needs to make another choice, the ultrasound system loops back and generates several new choices (506) from which the user may choose until the user is happy with the setting.

Method and Workflow for Frame Rate Enhancement

Figure 6:
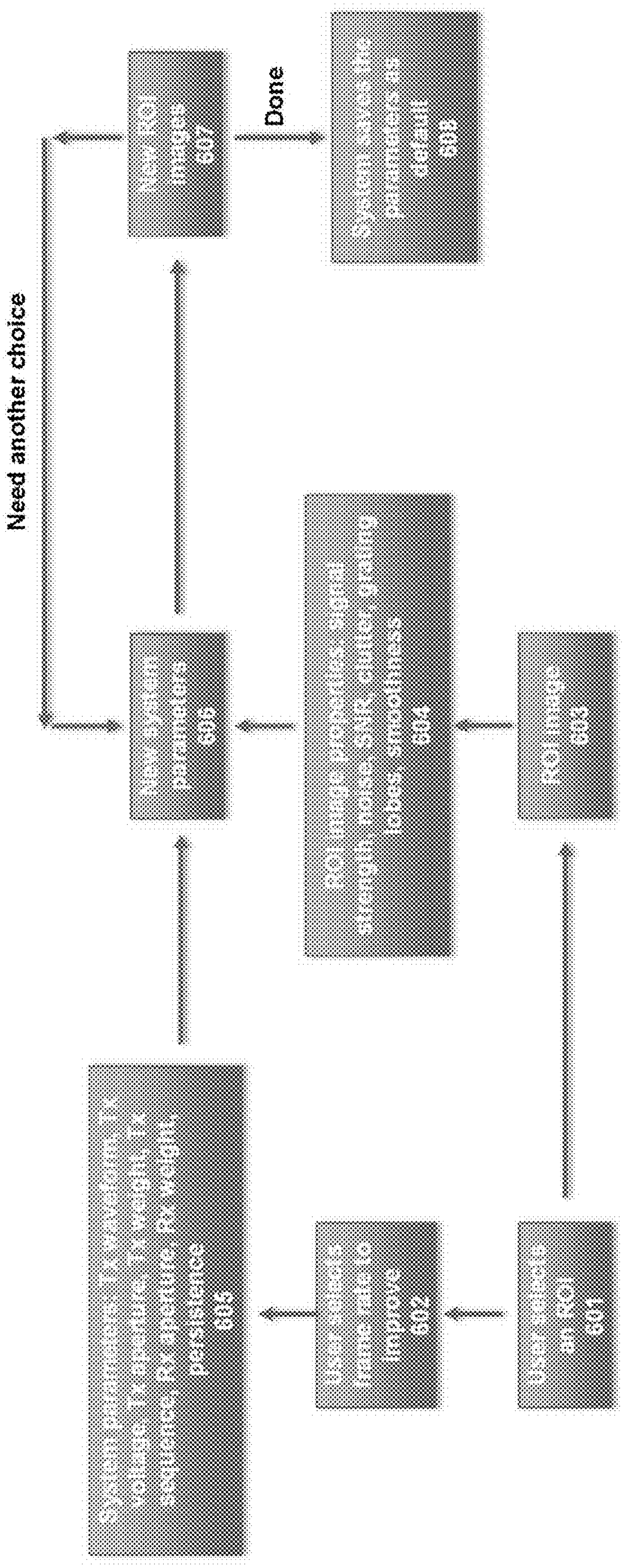
FIG. 6 illustrates some embodiments of a method and workflow for frame rate enhancement.

FIG. 6 illustrates some embodiments of a method and workflow for frame rate enhancement. Referring to FIG. 6, the user selects an ROI from an ultrasound image (601) and selects frame rate as the property to be enhanced (602).

In ultrasound imaging, the frame rate can be determined by the image size (depth and width) and how the image is generated (temporal and spatial sampling). From the image size perspective, if the system reduces the image width or depth, the frame rate can be increased. This is a straightforward method to increase frame rate if the ROI image is centered, and other regions in the total image are not important. While the system needs to know which part of the image is not essential, in some embodiments, the system learns based on the anatomy that is imaged. For example, if the clinicians are performing a nerve block procedure, the essential information in this case is the nerve and the needle path, and all or most other imaging regions are not relevant, and thus can be removed. In this case, the frame rate can get enhanced significantly.

From the imaging construction perspective, if the system reduces the temporal or spatial sampling, the frame rate can be enhanced accordingly. In some embodiments, the following parameters will impact the temporal sampling: the multibeam compounding method, persistence, etc. In some embodiments, the following parameters will impact the spatial sampling: the multi-line method, Tx sequence (including Tx waveform, aperture, and voltage), Rx configuration, etc. For example, the system can use more multi-lines or sparser line density to improve the frame rate. However, less sampling may lead to unsampled artifacts, and more multi-lines may lead to some multi-line artifacts. Hence, there are trade-offs between frame rate and image quality, and the system can analyze the current ROI image to evaluate current image quality. Then, based on the current image quality, the system can adjust certain parameters accordingly to improve (e.g., increase) the frame rate without perceptibly deteriorating image quality.

Referring to FIG. 6, after the user chooses frame rate to enhance 602) and after selecting the ROI (601), the system determines the following properties from the ROI image (603): signal strength, noise, SNR, clutter, grating lobes, and smoothness (604). The system also checks the current related parameters, such as, for example, Tx waveform, Tx voltage, Tx aperture, Tx weight, Tx sequence, Rx aperture, Rx weight, persistence (605). Based on the ROI image properties, the system determines the corresponding parameters to update and updates the system parameters based on the ROI image properties to create new system parameters (606). Using the new parameters, the ultrasound system generates new ROI images (607). If the user likes a new ROI image and makes a choice (e.g., selects an ROI image or a setting corresponding to the ROI image), the ultrasound system saves the setting as a new default (608). If the user needs to make another choice, the ultrasound system loops back and generates several new choices (606) from which the user may choose until the user is happy with the setting.

Method and Workflow for Color Sensitivity Enhancement

Figure 7:
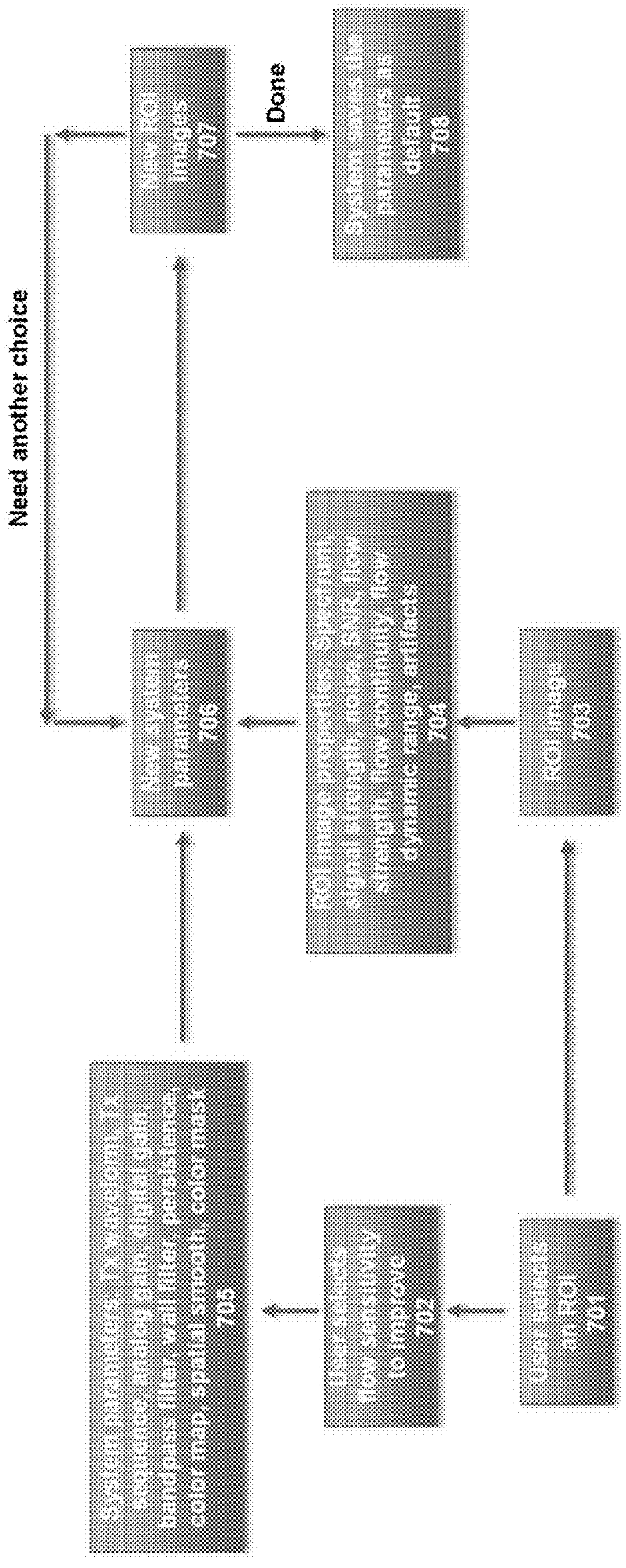
FIG. 7 illustrates some embodiments of a method and workflow for color sensitivity enhancement.

FIG. 7 illustrates some embodiments of a method and workflow for color sensitivity enhancement. Referring to FIG. 7, the user selects an ROI from an ultrasound image (701) and selects flow sensitivity (e.g., color flow sensitivity) as the property to be enhanced (702). Different from ultrasonic echo imaging, in color imaging, signal phase plays more important roles. However, to accurately extract phase information, signal strength should be higher than a certain level (e.g., SNR>6) so that the noise won't contaminate the determination of the signal phase. As shown in FIG. 7, in some embodiments, there are several system parameters that can impact the color sensitivity, such as Tx waveform, Tx sequence, gains (analog and digital gain), filters (bandpass filter and wall filter), persistence, color map, spatial smooth, and color mask. Changing one or more of the parameters above may increase color sensitivity with some trade-offs. For example, if the system updates Tx sequences to include more ensembles, the system increases the color sensitivity at the cost of reducing frame rate. Increasing gains can increase color sensitivity as well, but the artifacts may also get increased as well. Increasing spatial smooth can increase color sensitivity at the cost of lower spatial resolution. Therefore, in embodiments, the system can analyze the ROI color image first and determine the color image properties. Based on the ROI color image properties, the system can adjust one or more parameters to increase the color sensitivity without impacting other performance significantly. For example, if the frame rate is very fast to begin with, the system can increase the ensemble length to increase the color flow sensitivity.

Referring to FIG. 7, after the user chooses color sensitivity to enhance (702) and after selecting the ROI (701), the system determines the following properties from the ROI image (703): spectrum, signal strength, noise, SNR, flow strength, flow continuity, flow dynamic range, artifacts (704). The system also checks the current related parameters, such as, for example, Tx waveform, Tx sequence, analog gain, digital gain, bandpass filter, wall filter (that can remove the slow tissue motion), persistence, color map, spatial smooth, and color mask (705).

Based on the ROI image properties, the system determines the corresponding parameters to update and updates the system parameters based on the ROI image properties to create new system parameters (706). Using the new parameters, the ultrasound system generates new ROI images (707). If the user likes and makes a choice (e.g., selects an ROI image and/or a setting corresponding to an ROI image), the ultrasound system saves the setting as a new default (708). If the user needs to make another choice, the ultrasound system loops back and generates several new choices (706) from which the user may choose until the user is happy with the setting.

Method and Workflow for Any Local Feature Enhancement

Other than the features mentioned above, there are other local features that can be improved, such as, for example, but not limited to, color resolution, pulse-wave Doppler sensitivity, etc. For any feature, there are some system parameters that directly impact the feature performance, and some other system parameters can impact the feature indirectly. At times, a trade-off exists between features, for example, resolution versus penetration. Therefore, in some embodiments, when the system tries to improve one feature, the system does not decrease the performance of other features to such a level that the other feature becomes inacceptable. This requirement is why the system requires, for some embodiments, the user to select a ROI of the image to determine its properties. In other embodiments, the system can use a machine-learned model to determine the ROI. Once the system obtains the ROI image properties, the system can make adjustments accordingly. One example mentioned above is if the ROI image has a good SNR already, the system can increase the signal frequency to achieve better image resolution. In this case, the penetration will be reduced. The learning process can be another factor in the local feature enhancement process because the system can learn what the user prefers and then adjust the parameters accordingly.

Figure 8:
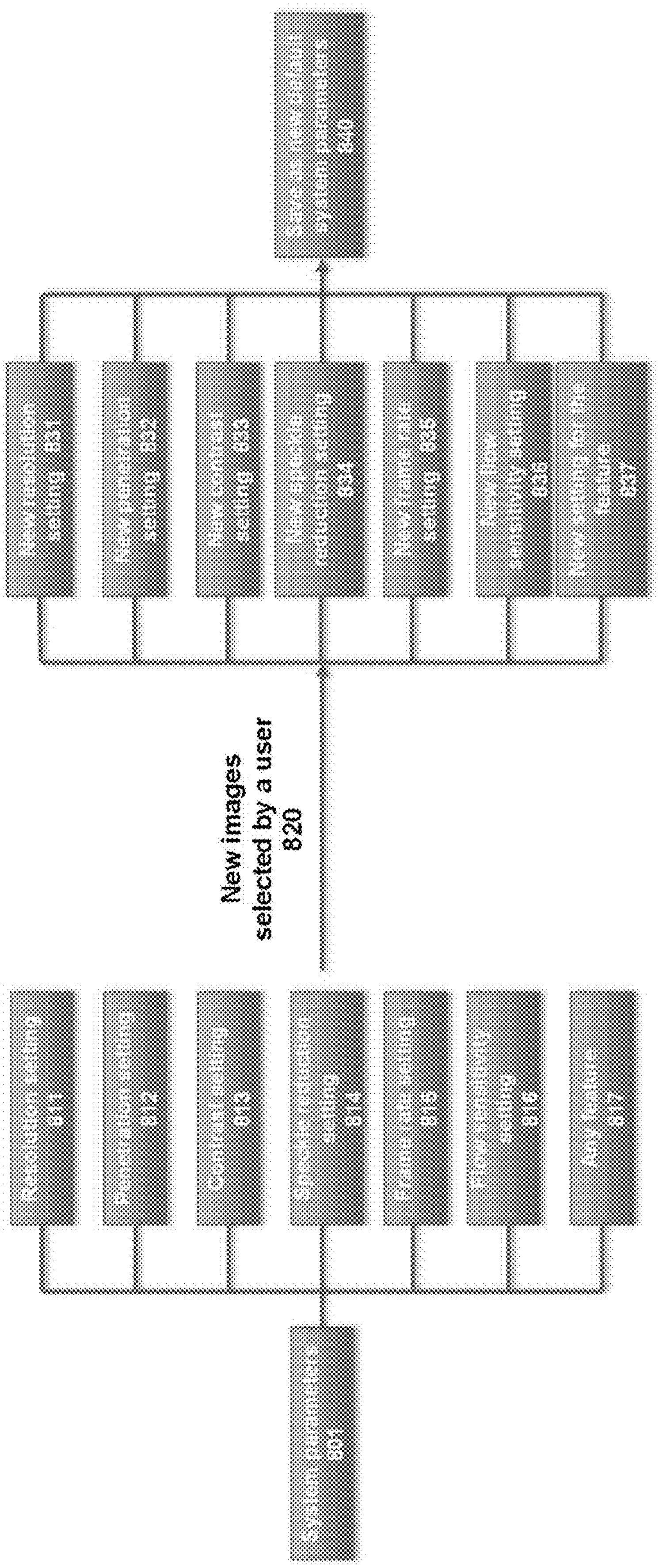
FIG. 8 illustrates some embodiments of a system learning process for feature enhancement.

FIG. 8 illustrates some embodiments of a system learning process for feature enhancement. Referring to FIG. 8, system parameters 801 include the resolution setting 811, penetration setting 812, contrast setting 813, speckle reduction setting 814, frame rate setting 815, flow sensitivity setting 816, and one or more other feature settings 817. The user selects new images generated by the system (820) based on changes to the settings made based on the user's chosen property for enhancement. These selections result in new settings determined by the system, including a new resolution setting 831, a new penetration setting 832, a new contrast setting 833, a new speckle reduction setting 834, a new frame rate setting 835, a new flow sensitivity setting 836, and one or more other new feature settings 837. The system saves these new settings as new default system parameters (840). As a result of the process, in some embodiments, eventually all the preferred settings can become the default settings for the users. The adaptation process to adjust the enhancement of local features can therefore be disabled or enabled by individual users, e.g., via a user interface, based on the default settings.

Note that in some embodiments, the enhancement process is iterative and allows the user to view multiple groups of enhanced ROIs from which the user may select an enhanced ROI that they desire and/or that meets their needs. In such a case, the user is able to interface with the system (e.g., through a user interface) to indicate their selections or control the system to present one or more additional groups of enhanced ROIs. Note that these multiple groups can have the same property that has been enhanced differently and/or different properties that have been enhanced.

User Interface Examples

In some embodiments, the system provides a user interface that includes aspects that are used during or as part of the feature enhancement process. In some embodiments, there are two parts of the UI design: a portion for user input and a portion to present the choices proposed by the system. For the user input, in some embodiments, the system includes an interface to enable the user to input selections and other information, including a dropdown menu for the user to choose what feature they want to enhance. In some embodiments, the system provides notifications to the user asking for a ROI to be drawn (or selected). In some embodiments, the user can directly draw the ROI on the image, e.g., via a touch screen of the ultrasound system. For the choices presented by the system, depending where the ROI is, the choices can be displayed right above the ROI, below the ROI, on the left of the ROI, on the right of the ROI, or combinations thereof. The choices displayed by the system can be three or four or any suitable number, depending on the feature to enhance. In aspects, a user can set via the user interface how many choices (e.g., ROI images) the system presents the user. Once the user selects a choice (e.g., by clicking on or selecting one of the ROI images suggested by the system), the system can refresh the entire image with the new settings and save the setting.

Figure 9B:
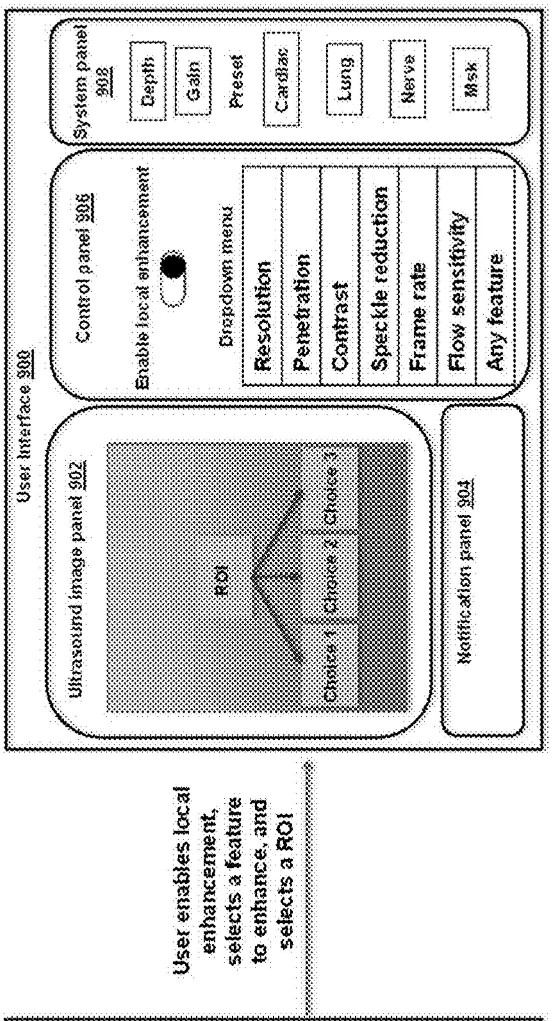
FIGS. 9A and 9B illustrate some embodiments of a user interface and user interaction.
Figure 9A:
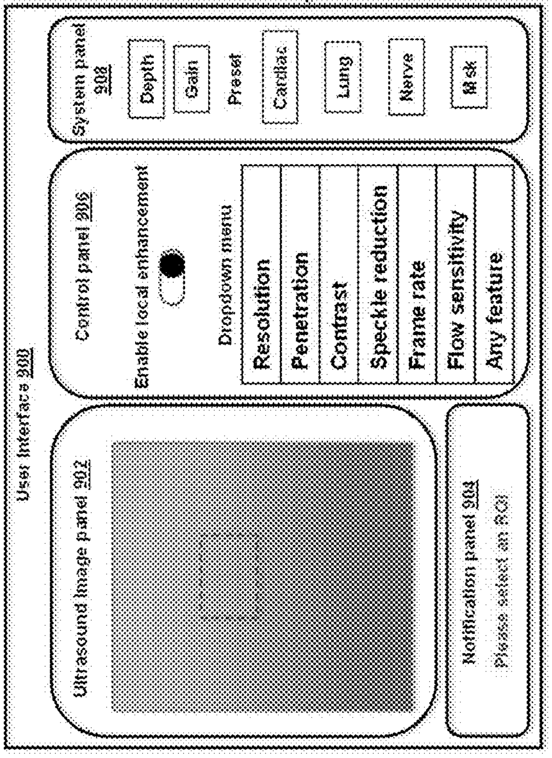

FIG. 9A illustrates an example user interface 900 to control the feature enhancement with the present invention. Referring to FIG. 9A, the user interface 900 can be displayed by any suitable device or component of an ultrasound system, such as an ultrasound probe, and ultrasound machine, a display device, etc. In some embodiments, the user interface 900 includes an ultrasound image panel 902, a notification panel 904, a feature enhancement method control panel 906, and an ultrasound system panel 908.

The ultrasound image panel 902 can display any suitable ultrasound image, such as a B-mode image, M-mode image, Doppler image, etc. The ultrasound image panel 902 can also provide users with a means to draw the ROI, e.g., with a stylus, finger, electronic drawing tool, etc., In some embodiments, the system allows the shape of the ROI to be any shape; in some other embodiments, the shape of the ROI is limited to one or more shapes (e.g., a rectangle, square, etc.). The notification panel 904 can display a notification when the user enables the local feature enhancement feature, such as “Please select an ROI”. The feature control panel 906 displays feature enable parameters and user-selectable control options about which feature to enhance.

Referring to FIG. 9B, after the users make the selection and draws or selects the ROI, in some embodiments, the user interface 900 can cause the ultrasound image panel 902 to present several choices for the user to choose. In some embodiments, the system causes the notification message in 904 to disappear, as illustrated in FIG. 9B. After the user selects a choice on panel 902, the system can refresh with the new image that is based on the settings determined from the user selection in the panel 902. In addition, the system saves the new parameters for future use, such as by setting a default configuration based on the new parameters (e.g., to include the new parameters).

In some embodiments, the ultrasound system panel 908 in FIGS. 9A and 9B includes any suitable controls and settings for controlling the ultrasound system, such as depth and gain adjustments, and a button to store images and/or video clips. The ultrasound system panel 908 can also include icons to select examination presets. These controls are meant to be exemplary and non-limiting.

Example Result of Method and Workflow for Resolution Enhancement

Figure 10A:
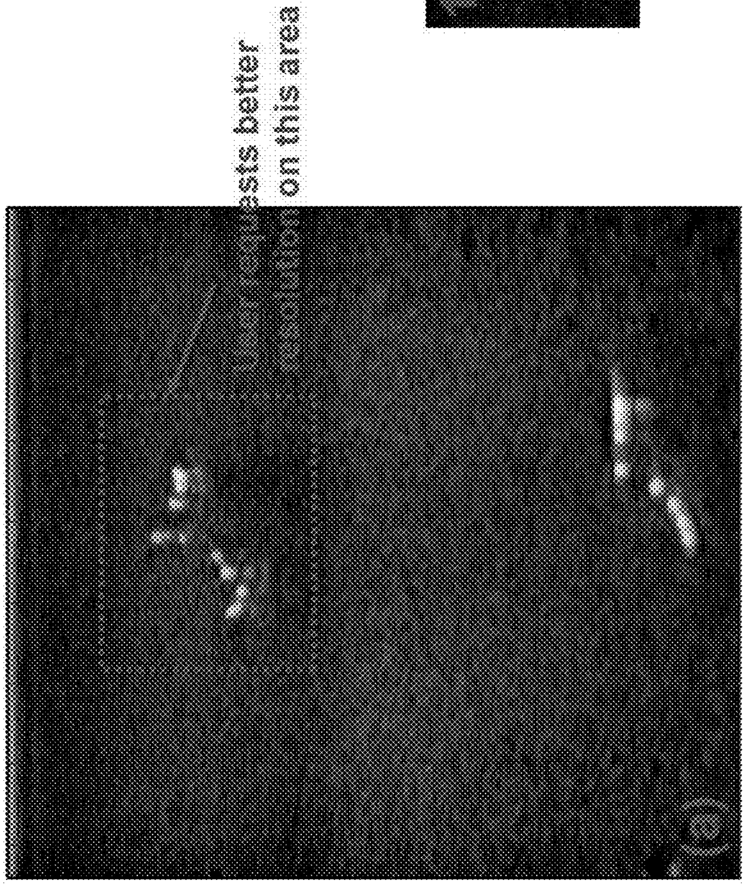
FIGS. 10A and 10B illustrate an example of a resolution enhancement result.
Figure 10B:
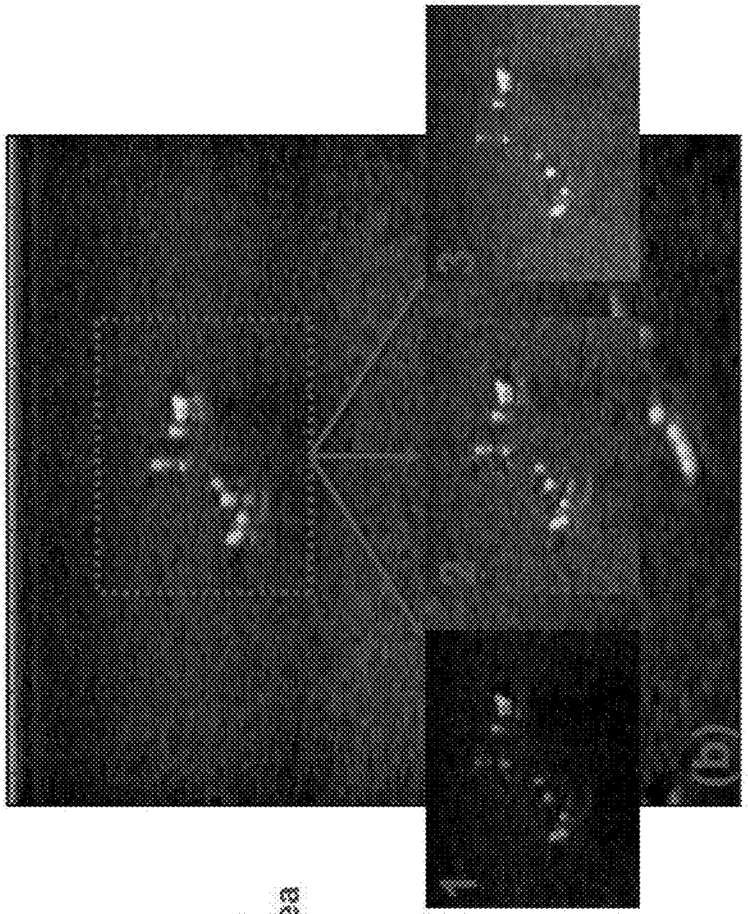

FIGS. 10A and 10B illustrate an example of a resolution enhancement results. After a user enables the local feature enhancement function, selects resolution to enhance, and selects a ROI in the image in FIG. 10A, in some embodiments, the system presents three choices in pop-up windows with better resolutions for the users to choose, as shown in FIG. 10B. Note that the three different choices can have different trade-offs and different settings of one or more parameters to increase the resolution. As shown in FIG. 10B, the first choice has much higher contrast than the other two choices, while the third choice has the highest enhancement result but with the least contrast. Therefore, the user can determine which enhanced image (e.g., ROI image) they deem as the best. After the user makes the choice, the system records the corresponding parameters and remembers the preference for this particular user. In some embodiments, when the same user uses the system the next time and images the same anatomy, the system can automatically use the parameters from this time.

Example Result of Method and Workflow for Penetration Enhancement

Figures 11A, 11B:
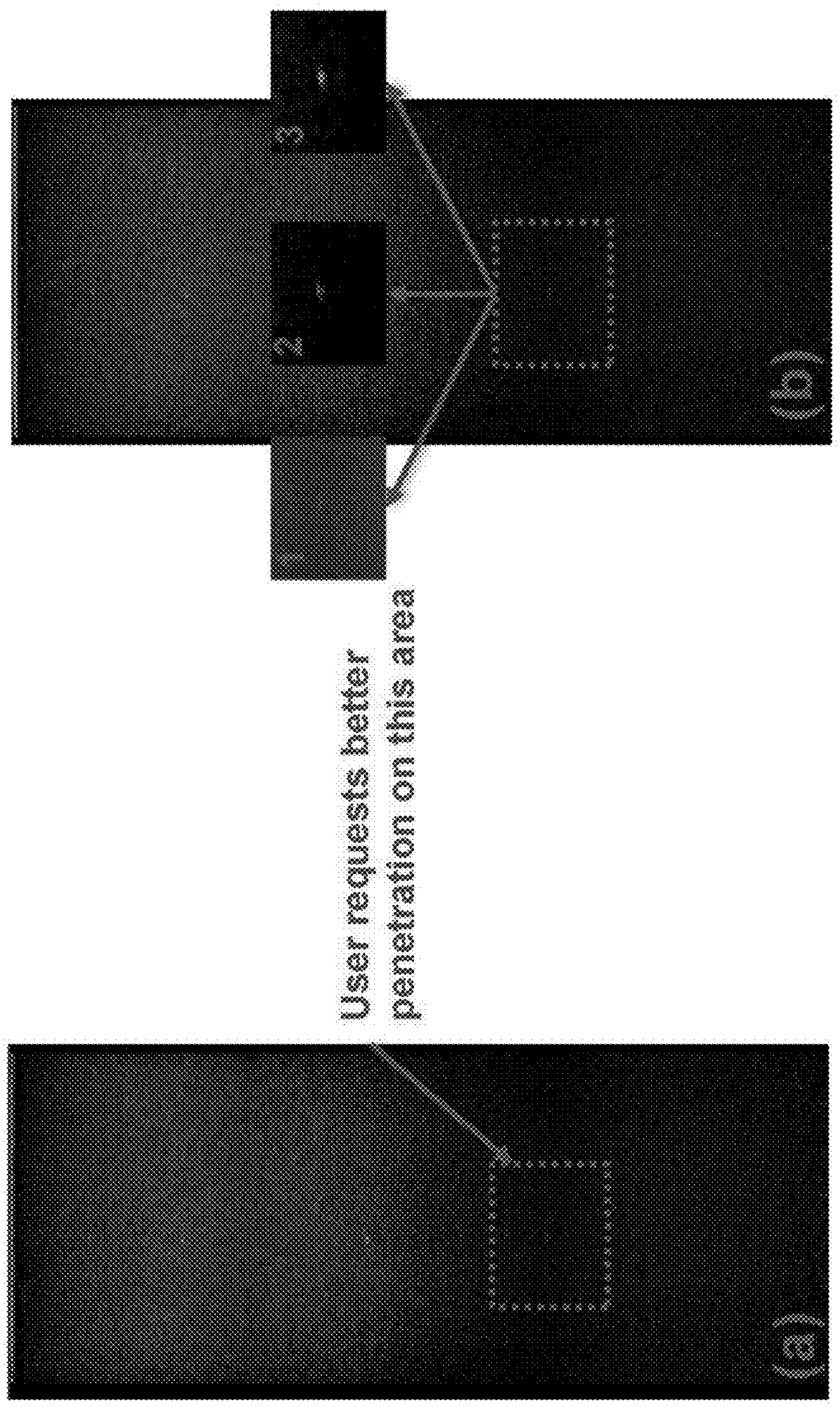
FIGS. 11A and 11B illustrate an example of a penetration enhancement result.

FIGS. 11A and 11B illustrate an example of penetration enhancement. After a user enables the local feature enhancement function, selects penetration to enhance, and selects a ROI in the image in FIG. 11A, in some embodiments, the system presents three choices in pop-up windows with better penetrations for the user to choose, as shown in FIG. 11B. Similar to the resolution case, the three different choices may have different trade-offs and different settings of one or more parameters to increase the penetration. As shown in FIG. 11B, the first choice has much smaller contrast than the other two choices, but with the least penetration enhancement. The third choice has the highest enhancement result but with the worst resolution. The user selects the one image which they determine is the best. After the user makes the choice, the system records the corresponding parameters (e.g., the settings used to generate the selected ROI image) and remembers the preference for this particular user. The next time (e.g., for a subsequent ultrasound examination), when the same user uses the system and images the same area, the system can automatically use the parameters from this time (e.g., a current ultrasound examination).

Example Result of Method and Workflow for Contrast Enhancement

Figure 12B:
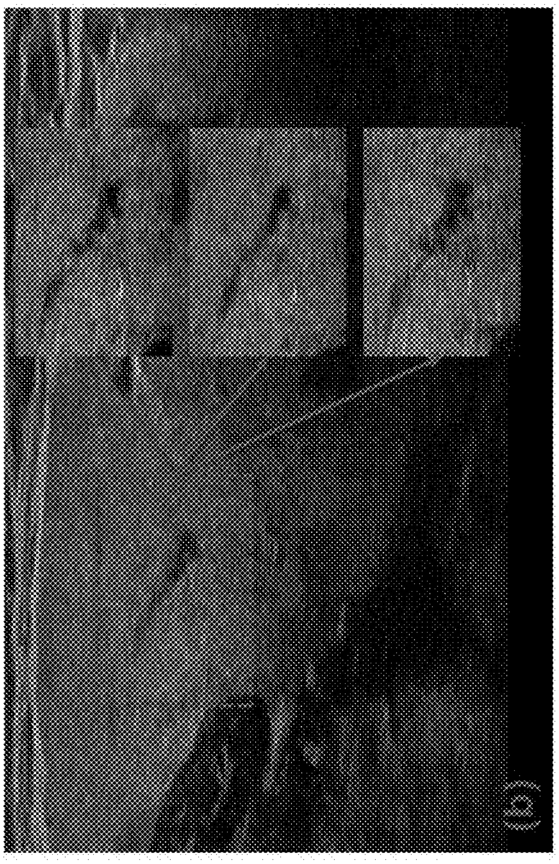
FIGS. 12A and 12B illustrate an example of a contrast enhancement result.
Figure 12A:

FIGS. 12A and 12B illustrate an example of contrast enhancement results. After a user enables the local feature enhancement function, selects contrast to enhance, and selects a ROI in the image in FIG. 12A, in some embodiments, the system presents three choices in pop-up windows with better contrast for the user to choose, as shown in FIG. 12B. The three different choices may have different trade-offs to increase the contrast. After the user makes the choice, the system records the corresponding parameters and remembers the preference for this user. The next time (e.g., for a subsequent ultrasound examination), when the same user uses the system and images the same area, the system can automatically use the parameters from this time (e.g., from a current ultrasound examination).

Example Result of Method and Workflow for Image Processing Enhancement

Figure 13A:
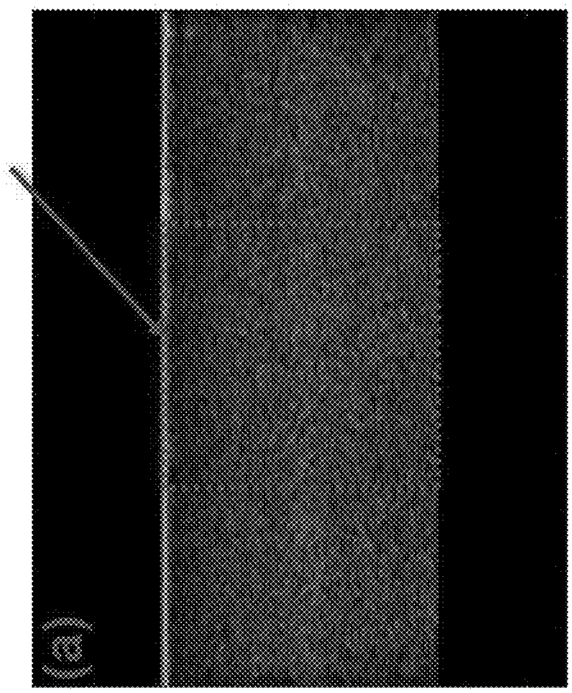
FIGS. 13A and 13B illustrate an example of an image processing enhancement result.
Figure 13B:
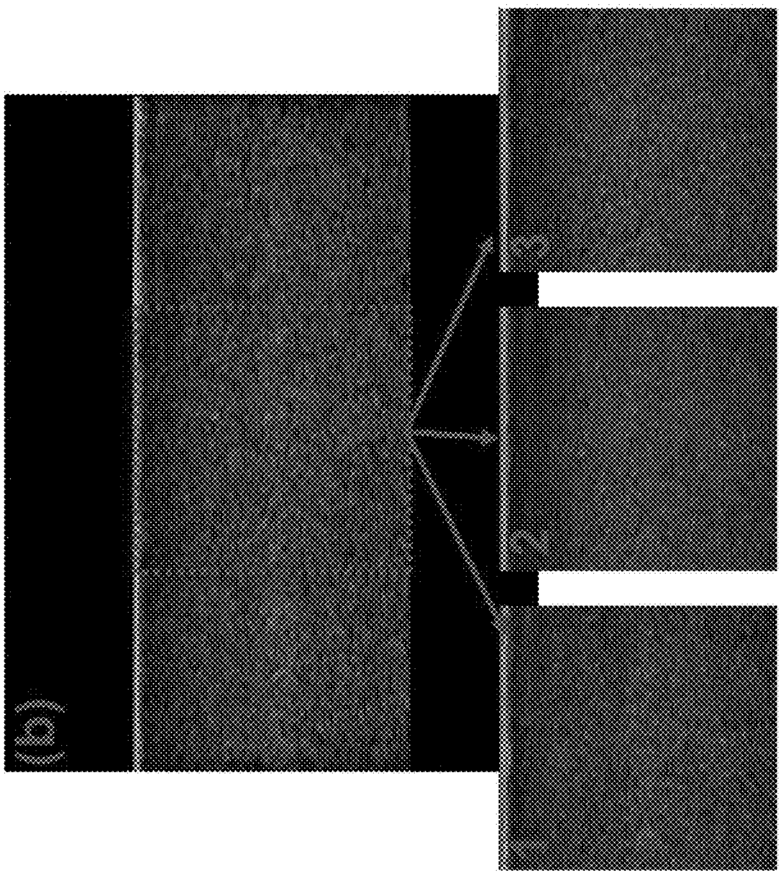

FIGS. 13A and 13B illustrate an example of image processing enhancement results. In this case, the users would like to have smaller grain size in the selected area. After a user enables the local feature enhancement function, selects contrast to enhance, and selects a ROI in the image in FIG. 13A, in some embodiments, the system presents three choices in pop-up windows with smaller grain size for the users to choose, as shown in FIG. 13B. The three different choices may have different trade-offs and different settings of one or more parameters to reduce the grain size. After the user makes the choice, the system records the corresponding parameters and remembers the preference of this user. The next time (e.g., for a subsequent ultrasound examination), when the same user uses the system and images the same area, the system automatically uses the parameters from this time (e.g., from a current ultrasound examination).

Example Result of Method and Workflow for Frame Rate Enhancement

Figure 14B:
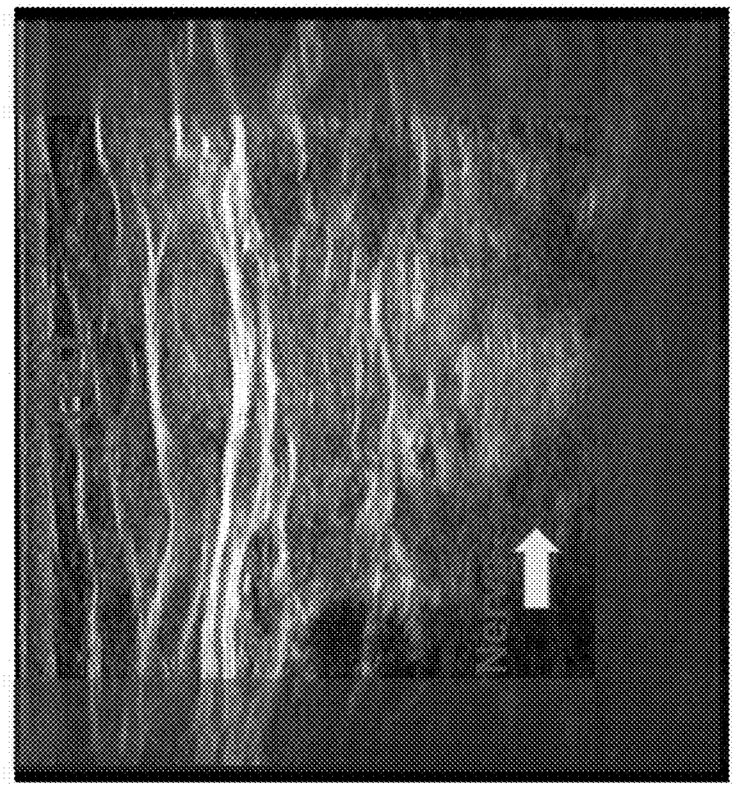
FIGS. 14A and 14B illustrate an example of a frame rate enhancement result.
Figure 14A:
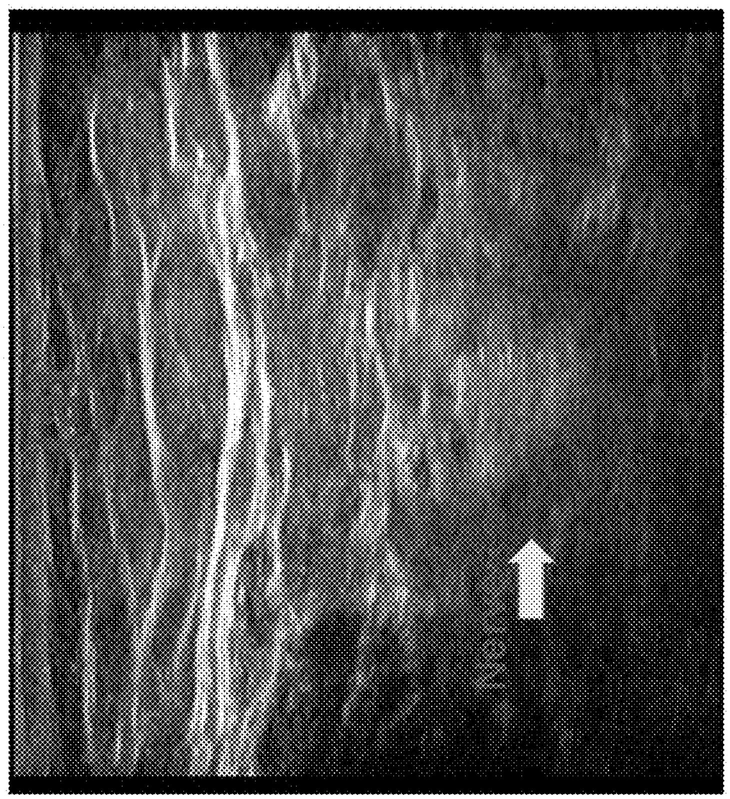

FIGS. 14A and 14B illustrate an example of frame rate enhancement results. This enhancement is different from others, because it is a frame rate increase, which may not be easy to present with small images (e.g., show in the pop-up small images). In this case, the system can determine which parameters to adjust based on the overall image and the applications. In this example, the clinician is trying to image a for local anesthesia. Therefore, one way to increase frame rate is to crop these areas that are not useful for the procedure, as shown in the red area in FIG. 14B. In some other embodiments, the system still presents the enhanced images like the other feature enhancement with multiple choices. The procedure and results are similar to that already shown in the previous examples.

Example Result of Method and Workflow for Color Flow Sensitivity Enhancement

Figure 15B:
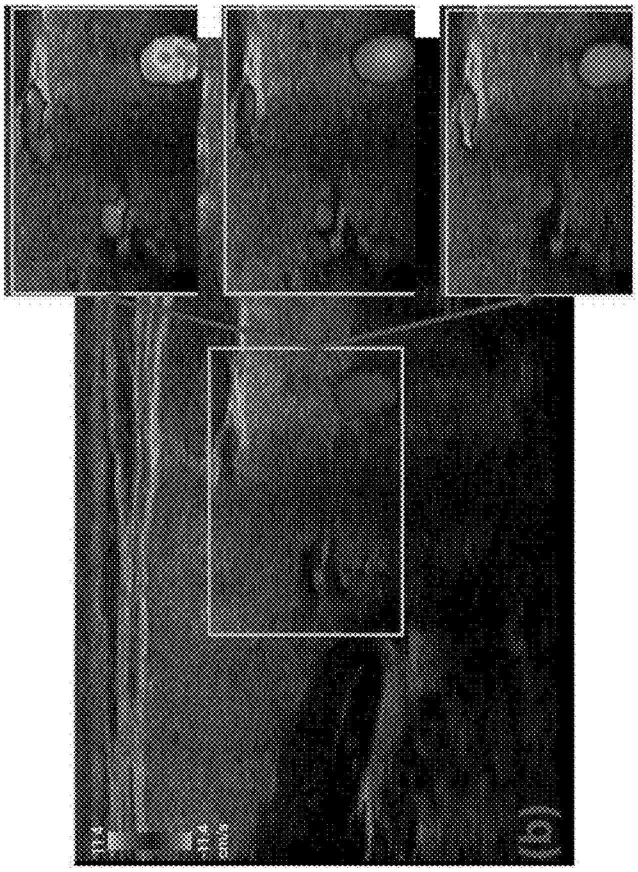
FIGS. 15A and 15B illustrate an example of a color flow sensitivity enhancement result.
Figure 15A:

FIGS. 15A and 15B illustrate an example of color flow sensitivity enhancement. In this case, the user would like to have better color sensitivity in the selected area. After the user enables the local feature enhancement function, selects color sensitivity to enhance, and selects a ROI in the image as shown in FIG. 15A, in some embodiments, the system presents three choices in pop-up windows with better color sensitivity for the users to choose, as shown in FIG. 15B. The three different choices may have different trade-offs and different settings of one or more parameters to increase the color sensitivity. After the users make the choice, the system records the corresponding parameters and remembers the preference of this user. Next time (e.g., for a subsequent ultrasound examination), when the same user uses the system and image the same area, the system can automatically use the parameters from this time (e.g., a current ultrasound examination).

Example Procedures

Figure 16A:
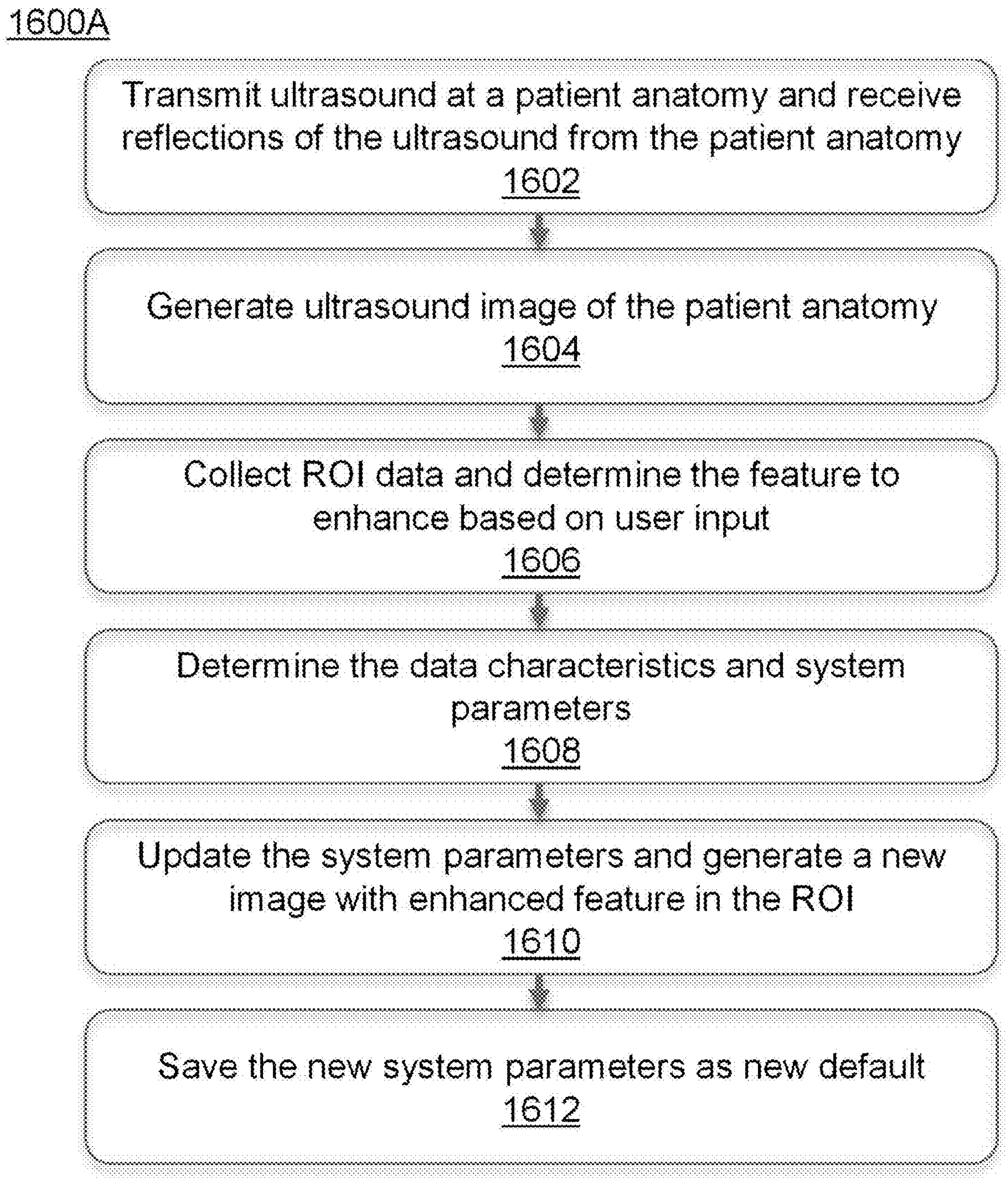
FIGS. 16A-16D illustrate some embodiments of a procedure for a local feature enhancement method.
Figure 17:
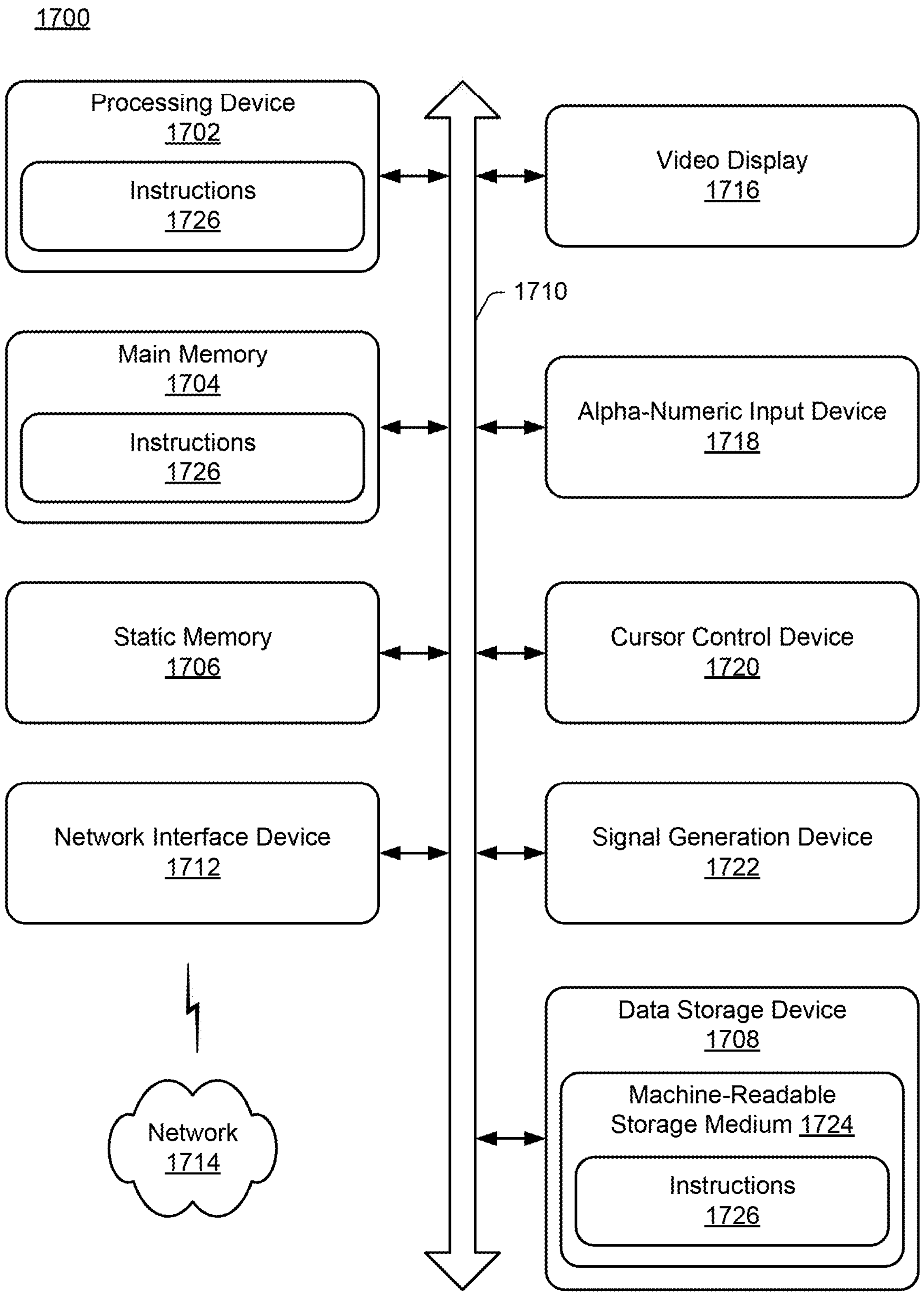
FIG. 17 illustrates a block diagram of an example computing device that can perform one or more of the operations described herein, in accordance with some implementations.

FIG. 16A illustrates some embodiments of a method 1600A that can be implemented by an ultrasound system for local feature enhancement in ultrasound images. The ultrasound system can include an ultrasound scanner (e.g., transducer or probe), an ultrasound machine, a processor system, and a display device. In some embodiments, the ultrasound system includes a computing device having processing logic that can include hardware (e.g., circuitry, dedicated logic, memory, etc.), software (such as is run on a general-purpose computer system or a dedicated machine), firmware (e.g., software programmed into a read-only memory), or combinations thereof. In some embodiments, the process is performed by one or more processors of a computing device such as, for example, but not limited to, an ultrasound machine with an ultrasound imaging subsystem. In some embodiments, the computing device is represented by a computing device as shown in FIG. 17.

Referring to FIG. 16A, ultrasound is transmitted at a patient anatomy and reflections of the ultrasound from the patient anatomy are received (block 1602). An ultrasound image is generated based on received data (block 1604). A ROI in the image is selected and a feature to enhance is determined based on user input (block 1606). Here, there can be one or more users. Based on the ROI image, the data characteristics and corresponding system parameters are determined (block 1608). The system prepares several choices for the user to choose. After the users make a choice, the system parameters are updated, and a new image is generated with at least one enhanced feature in ROI (block 1610). The system saves the new parameters and use them as default for the future case (block 1612).

Figure 16B:
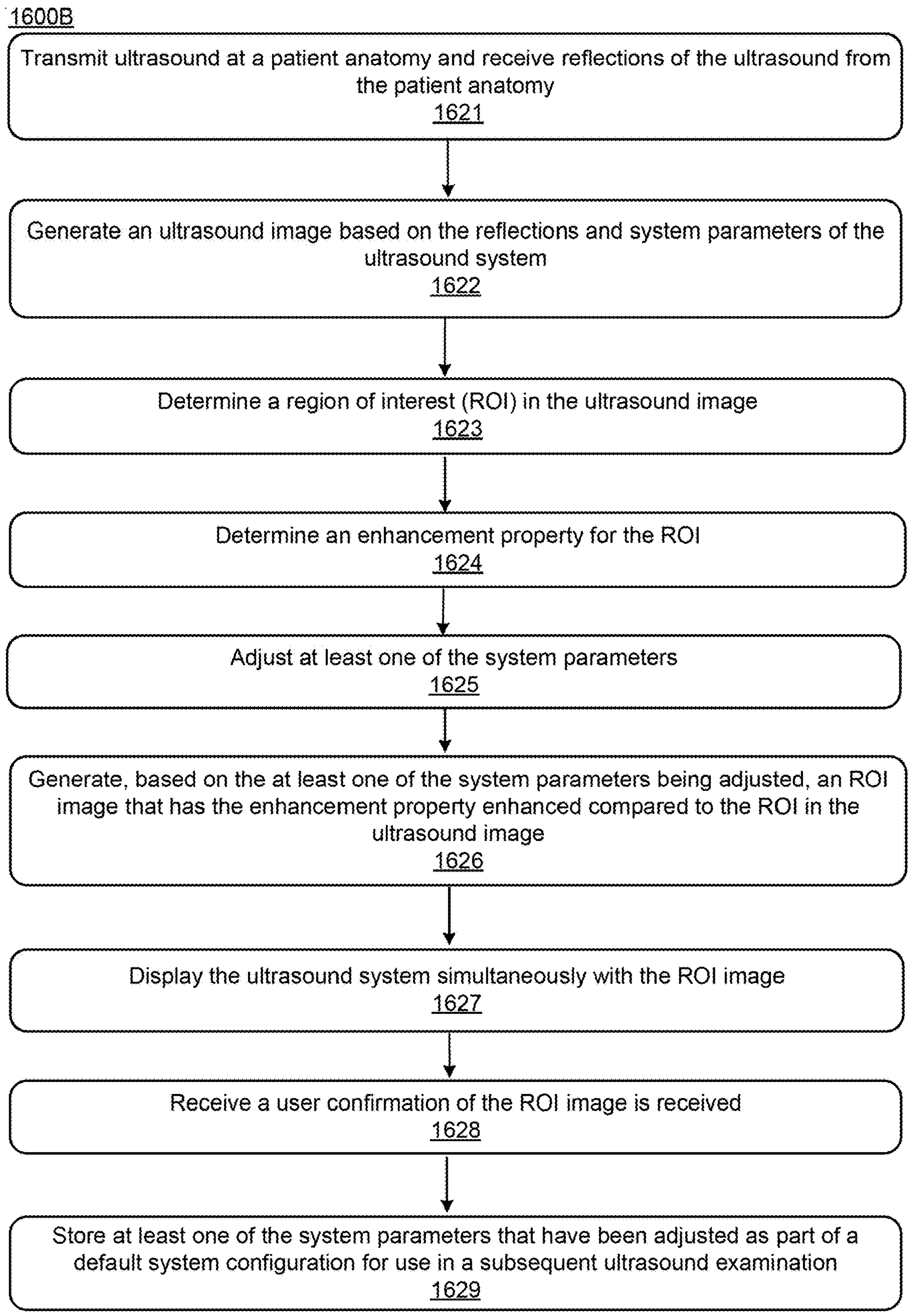

FIG. 16B illustrates some embodiments of a method 1600B that can be implemented by an ultrasound system for local feature enhancement in ultrasound images. The ultrasound system can include an ultrasound scanner (e.g., transducer or probe), an ultrasound machine, a processor system, and a display device. In some embodiments, the ultrasound system includes a computing device having processing logic that can include hardware (e.g., circuitry, dedicated logic, memory, etc.), software (such as is run on a general-purpose computer system or a dedicated machine), firmware (e.g., software programmed into a read-only memory), or combinations thereof. In some embodiments, the process is performed by one or more processors of a computing device such as, for example, but not limited to, an ultrasound machine with an ultrasound imaging subsystem. In some embodiments, the computing device is represented by a computing device as shown in FIG. 17.

Referring to FIG. 16B, ultrasound is transmitted at a patient anatomy and reflections of the ultrasound are received from the patient anatomy (block 1621). A processor system generates an ultrasound image is generated based on the reflections and system parameters of the ultrasound system (block 1622), determines a region of interest (ROI) in the ultrasound image (block 1623), determines an enhancement property for the ROI (block 1624), and adjusts at least one of the system parameters (block 1625). In some embodiments, the determination of the ROI in the ultrasound image is based on receiving a user selection of the ROI in the ultrasound image. In some other embodiments, the processor system is configured to implement a machine-learned model to determine the ROI in the ultrasound image.

In some embodiments, the enhancement property is selected from the group consisting of resolution, penetration, contrast, speckle reduction, frame rate, flow resolution, flow density, and color sensitivity. In some embodiments, the determination of the enhancement property for the ROI includes receiving a user selection of the enhancement property. In some embodiments, the processor system is configured to implement a machine-learned model to determine the enhancement property for the ROI.

In some embodiments, the processor system determines a ROI image property for the ROI in the ultrasound image, and the adjustment of the at least one of the system parameters is based on the ROI image property. In some embodiments, the ROI image property is selected from the group consisting of a spectrum, a signal strength, a noise level, a signal-to-noise ratio, a brightness, a resolution, a clutter, grating lobes, artifacts, a dynamic range, a uniformity, an edge definition, a smoothness, a line connectivity, hole fillings, a flow strength, a flow continuity, and a flow dynamic range.

In some embodiments, at least one of the system parameters includes one or more of a transmit waveform, a transmit voltage, a transmit aperture, an analog gain, a digital gain, an analog-to-digital converter cutoff frequency, a dynamic range, a filter bandwidth, a compression curve, a persistence, a receive aperture, a receive weight, a color map, a color mask, and beam compounding parameters.

Based on the at least one of the system parameters being adjusted, ROI image is generated that has the enhancement property enhanced compared to the ROI in the ultrasound image (block 1626). Thereafter, the ultrasound system is displayed simultaneously with the ROI image (block 1627).

In some embodiments of the method 1600B, a user confirmation of the ROI image is received (block 1628) and at least one of the system parameters that have been adjusted are stored as part of a default system configuration for use in a subsequent ultrasound examination (1629). In some embodiments, these system parameters are stored using a memory storage device. In some embodiments, storing system parameters occurs in response to responsive to the user confirmation. In some embodiments, the display device is implemented to receive a user selection that refuses the ROI image, and an additional adjustment is made and the additional ROI image responsive to the user selection is generated.

In some embodiments, an adjustment value for the adjustment of the at least one of the system parameters from a memory storage device is obtained as part of a current ultrasound examination. The adjustment value obtained from the memory storage device could have been determined as part of a previous ultrasound examination.

In some other embodiments of the method 1600B, an additional enhancement property for the ROI is obtained and an additional ROI image having the additional enhancement property enhanced compared to the ROI in the ultrasound image is obtained. This additional ROI image with the additional enhancement property enhanced can be displayed simultaneously display the ultrasound image and the ROI image.

In still some other embodiments of the method 1600B, an additional adjustment to the at least one of the system parameters or another of the system parameters is made, an additional ROI image having the enhancement property enhanced compared to the ROI in the ultrasound image is generated based on the additional adjustment, and the ultrasound image, the ROI image, and the additional ROI image are displayed simultaneously. These operations can be performed by the processor system of the ultrasound system.

Figure 16C:
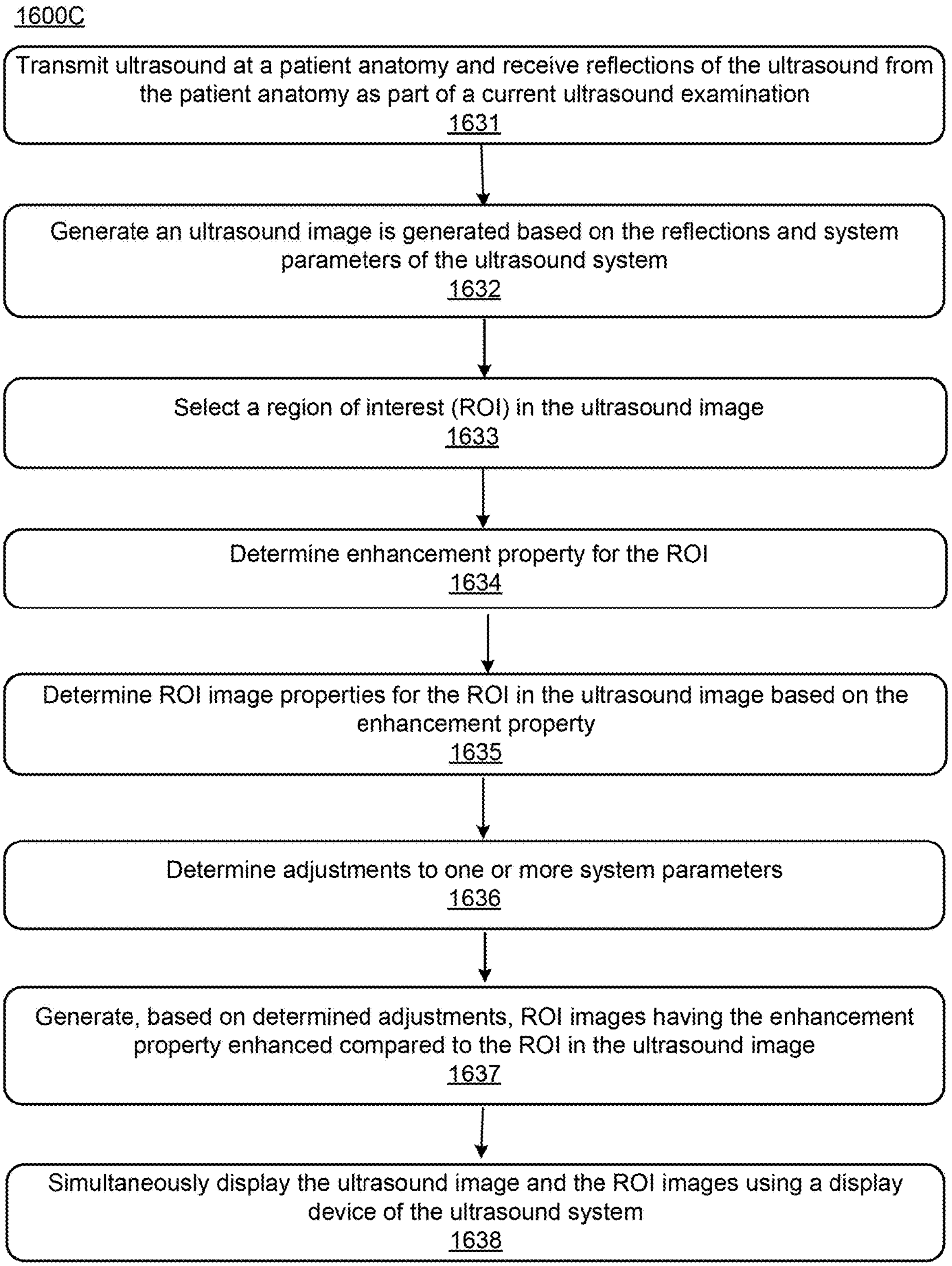

FIG. 16C illustrates some embodiments of a method 1600C that can be implemented by an ultrasound system for local feature enhancement in ultrasound images. The ultrasound system can include an ultrasound scanner (e.g., transducer or probe), an ultrasound machine, a processor system, and a display device. In some embodiments, the ultrasound system includes a computing device having processing logic that can include hardware (e.g., circuitry, dedicated logic, memory, etc.), software (such as is run on a general-purpose computer system or a dedicated machine), firmware (e.g., software programmed into a read-only memory), or combinations thereof. In some embodiments, the process is performed by one or more processors of a computing device such as, for example, but not limited to, an ultrasound machine with an ultrasound imaging subsystem. In some embodiments, the computing device is represented by a computing device as shown in FIG. 17.

Referring to FIG. 16C, method 1600C starts with transmitting ultrasound at a patient anatomy and receiving reflections of the ultrasound from the patient anatomy as part of a current ultrasound examination (block 1631). In some embodiments, the transmission of ultrasound and reception of its reflections is performed by a scanner of the ultrasound system.

Next, an ultrasound image is generated based on the reflections and system parameters of the ultrasound system (block 1632) and a region of interest (ROI) in the ultrasound image is selected (block 1633). Once the ROI has been selected, an enhancement property for the ROI is determined (block 1634). In some embodiments, the enhancement property includes a spatial resolution, the ROI image properties include a lateral resolution and an axial resolution. In some other embodiments, the enhancement property includes a penetration, the ROI image properties include a signal strength and a brightness.

After determining the enhancement property, ROI image properties for the ROI in the ultrasound image are determined based on the enhancement property (block 1635) and adjustments to those system parameters are determined (block 1636). In some embodiments, the adjustments correspond to the ROI image properties. In some embodiments, the one or more of the system parameters include at least one of an analog gain, a digital gain, and a transmit frequency. In some other embodiments, these system parameters include at least one of a transmit frequency and a compression curve.

Next, ROI images having the enhancement property enhanced compared to the ROI in the ultrasound image are generated based on the adjustments (block 1637). In some embodiments, the ROI images exclude image content of the ultrasound image that is not contained in the ROI.

After enhancement, the ultrasound image and the ROI images are simultaneously displayed using a display device of the ultrasound system (block 1638). In some embodiments, the display device is implemented to receive a user selection of one of the ROI images, and the processor system is implemented to cause the adjustments to the one or more of the system parameters that correspond to the one of the ROI images to be stored in a memory storage device for use in a subsequent ultrasound examination.

Figure 16D:
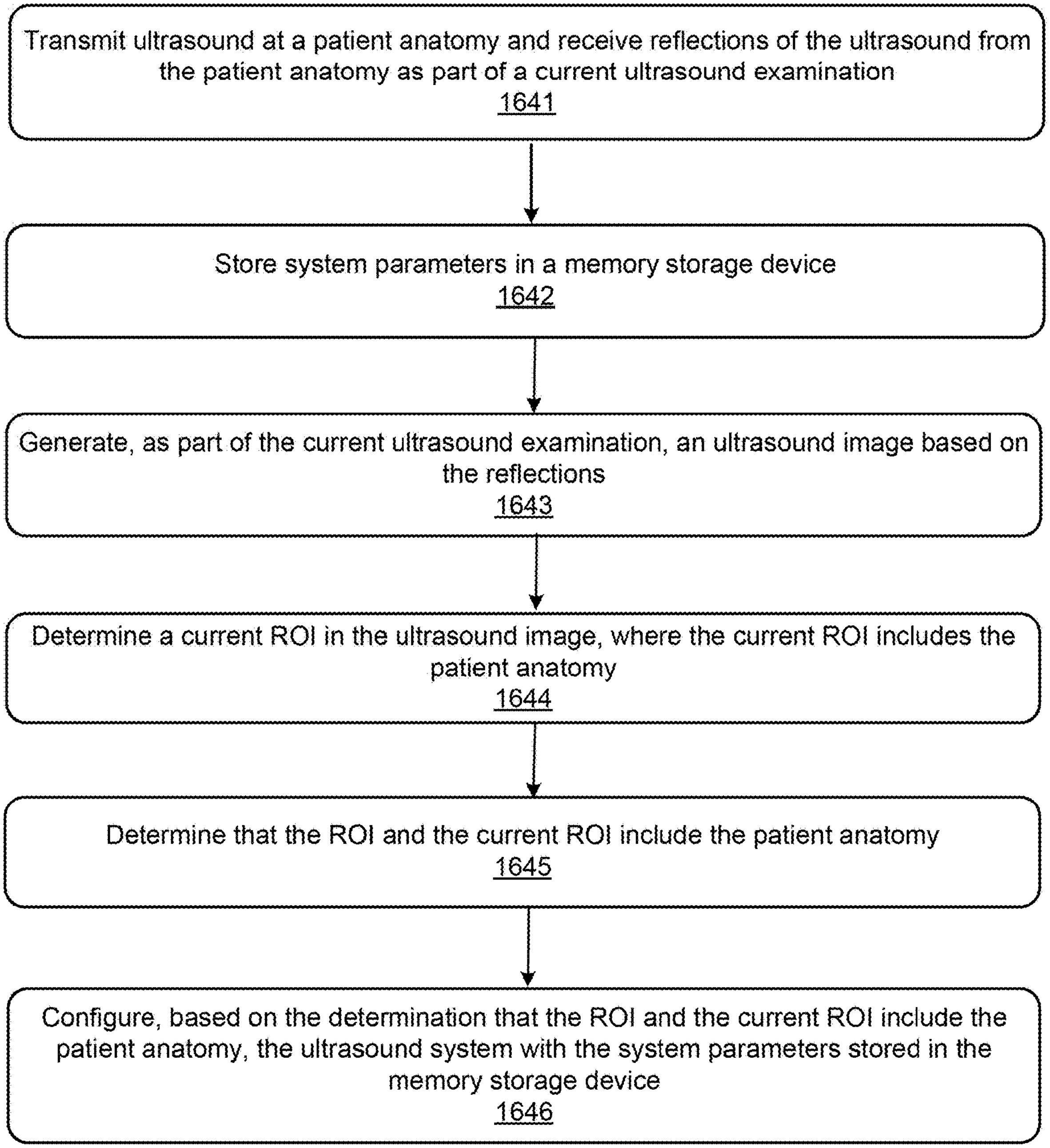

FIG. 16D illustrates some embodiments of a method 1600D that can be implemented by an ultrasound system for local feature enhancement in ultrasound images. The ultrasound system can include an ultrasound scanner (e.g., transducer or probe), an ultrasound machine, a processor system, and a display device. In some embodiments, the ultrasound system includes a computing device having processing logic that can include hardware (e.g., circuitry, dedicated logic, memory, etc.), software (such as is run on a general-purpose computer system or a dedicated machine), firmware (e.g., software programmed into a read-only memory), or combinations thereof. In some embodiments, the process is performed by one or more processors of a computing device such as, for example, but not limited to, an ultrasound machine with an ultrasound imaging subsystem. In some embodiments, the computing device is represented by a computing device as shown in FIG. 17.

Referring to FIG. 16D, method 1600D starts with transmitting ultrasound at a patient anatomy and receiving reflections of the ultrasound from the patient anatomy as part of a current ultrasound examination (block 1641). In some embodiments, the transmission of ultrasound and reception of its reflections is performed by a scanner of the ultrasound system.

System parameters are stored in a memory storage device (block 1642). In some embodiments, the system parameters are determined during a previous ultrasound examination, to enhance an enhancement property in a region of interest (ROI) in a previous ultrasound image generated during the previous ultrasound examination.

As part of the current ultrasound examination, a processor system generates an ultrasound image based on the reflections (block 1643), determines a current ROI in the ultrasound image, where the current ROI includes the patient anatomy (block 1644), and determines that the ROI and the current ROI include the patient anatomy (block 1645).

Based on the determination that the ROI and the current ROI include the patient anatomy, the ultrasound system is configured with the system parameters stored in the memory storage device (block 1646). In some embodiments, the processor system is implemented to receive a user selection of the enhancement property, and configuring the ultrasound system with the system parameters is also based on the user selection.

An Example Device

FIG. 17 illustrates a block diagram of some embodiments of a computing device 1700 that can perform one or more of the operations described herein. The computing device 1700 can be connected to other computing devices in a local area network (LAN), an intranet, an extranet, and/or the Internet.

The computing device can operate in the capacity of a server machine in a client-server network environment or in the capacity of a client in a peer-to-peer network environment. The computing device can be provided by a personal computer (PC), a server computer, a desktop computer, a laptop computer, a tablet computer, a smartphone, an ultrasound machine, or any machine capable of executing a set of instructions (sequential or otherwise) that specify actions to be taken by that machine. Further, while only a single computing device is illustrated, the term "computing device" shall also be taken to include any collection of computing devices that individually or jointly execute a set (or multiple sets) of instructions to perform the methods discussed herein. In some embodiments, the computing device 1700 is one or more of an ultrasound machine, an ultrasound scanner, an access point, and a packet-forwarding component.

The example computing device 1700 can include a processing device 1702 (e.g., a general-purpose processor, a programmable logic device (PLD), etc.), a main memory 1704 (e.g., synchronous dynamic random-access memory (DRAM), read-only memory (ROM), etc.), and a static memory 1706 (e.g., flash memory, a data storage device 1708, etc.), which can communicate with each other via a bus 1710. The processing device 1702 can be provided by one or more general-purpose processing devices such as a microprocessor, a central processing unit, or the like. In some embodiments, the processing device 1702 comprises a complex instruction set computing (CISC) microprocessor, a reduced instruction set computing (RISC) microprocessor, a very long instruction word (VLIW) microprocessor, or a processor implementing other instruction sets or processors implementing a combination of instruction sets. The processing device 1702 can also comprise one or more special-purpose processing devices such as an application-specific integrated circuit (ASIC), a field programmable gate array (FPGA), a digital signal processor (DSP), a network processor, or the like. The processing device 1702 can be configured to execute the operations described herein, in accordance with one or more aspects of the present disclosure, for performing the operations and steps discussed herein.

The computing device 1700 can further include a network interface device 1712, which can communicate with a network 1714. The computing device 1700 also can include a video display unit 1716 (e.g., a liquid crystal display (LCD), an organic light-emitting diode (OLED), a cathode ray tube (CRT), etc.), an alphanumeric input device 1718 (e.g., a keyboard), a cursor control device 1720 (e.g., a mouse), and an acoustic signal generation device 1722 (e.g., a speaker, a microphone, etc.). In one embodiment, the video display unit 1716, the alphanumeric input device 1718, and the cursor control device 1720 can be combined into a single component or device (e.g., an LCD touch screen).

The data storage device 1708 can include a computer-readable storage medium 1724 on which can be stored one or more sets of instructions 1726 (e.g., instructions for carrying out the operations described herein, in accordance with one or more aspects of the present disclosure). The instructions 1726 can also reside, completely or at least partially, within the main memory 1704 and/or within the processing device 1702 during execution thereof by the computing device 1700, where the main memory 1704 and the processing device 1702 also constitute computer-readable media. The instructions can further be transmitted or received over the network 1714 via the network interface device 1712.

The systems, devices, and procedures disclosed herein constitute numerous advantages over convention ultrasound systems, devices, and procedures, including allowing a clinician to improve and enhance, and potentially optimize against the clinician's preferences, images at regions of interest as opposed to being limited to images generated based on general settings that are applied to many patients. Furthermore, the clinician is able to avoid being constrained with settings designed to provide benefits to the image overall instead of particular areas that are more important for particular use case. Using the techniques herein, a clinician can select one or more settings that can be tailored to an individual patient as well as the clinician's individual preferences (e.g., examination preferences, etc.). In this manner, regardless of the unique characteristics of a patient, ultrasound images can be generated that are useful to a clinician for particular use cases, and not be limited to ultrasound images that have poor resolution, result from poor penetration and/or contrast.

Moreover, the techniques disclosed herein allow a system to operate more efficiently as desired enhancements do not need to be performed on the areas of the ultrasound image that are not important to a clinician, thereby reducing the ultrasound system acquisition and computation resources.

Various techniques are described in the general context of software, hardware elements, or program modules. Generally, such modules include routines, programs, objects, elements, components, data structures, and so forth that perform particular tasks or implement particular abstract data types. The terms "module," "functionality," and "component" as used herein generally represent software, firmware, hardware, or a combination thereof. In some aspects, the modules described herein are embodied in the data storage device 1708 of the computing device 1700 as executable instructions or code. Although represented as software implementations, the described modules can be implemented as any form of a control application, software application, signal-processing and control module, hardware, or firmware installed on the computing device 1700.

While the computer-readable storage medium 1724 is shown in an illustrative example to be a single medium, the term "computer-readable storage medium" should be taken to include a single medium or multiple media (e.g., a centralized or distributed database and/or associated caches and servers) that store the one or more sets of instructions. The term "computer-readable storage medium" shall also be taken to include any medium that is capable of storing, encoding, or carrying a set of instructions for execution by the machine and that causes the machine to perform the methods described herein. The term "computer-readable storage medium" shall accordingly be taken to include, but not be limited to, solid-state memories, optical media, and magnetic media.

An Example Environment

Figure 18:
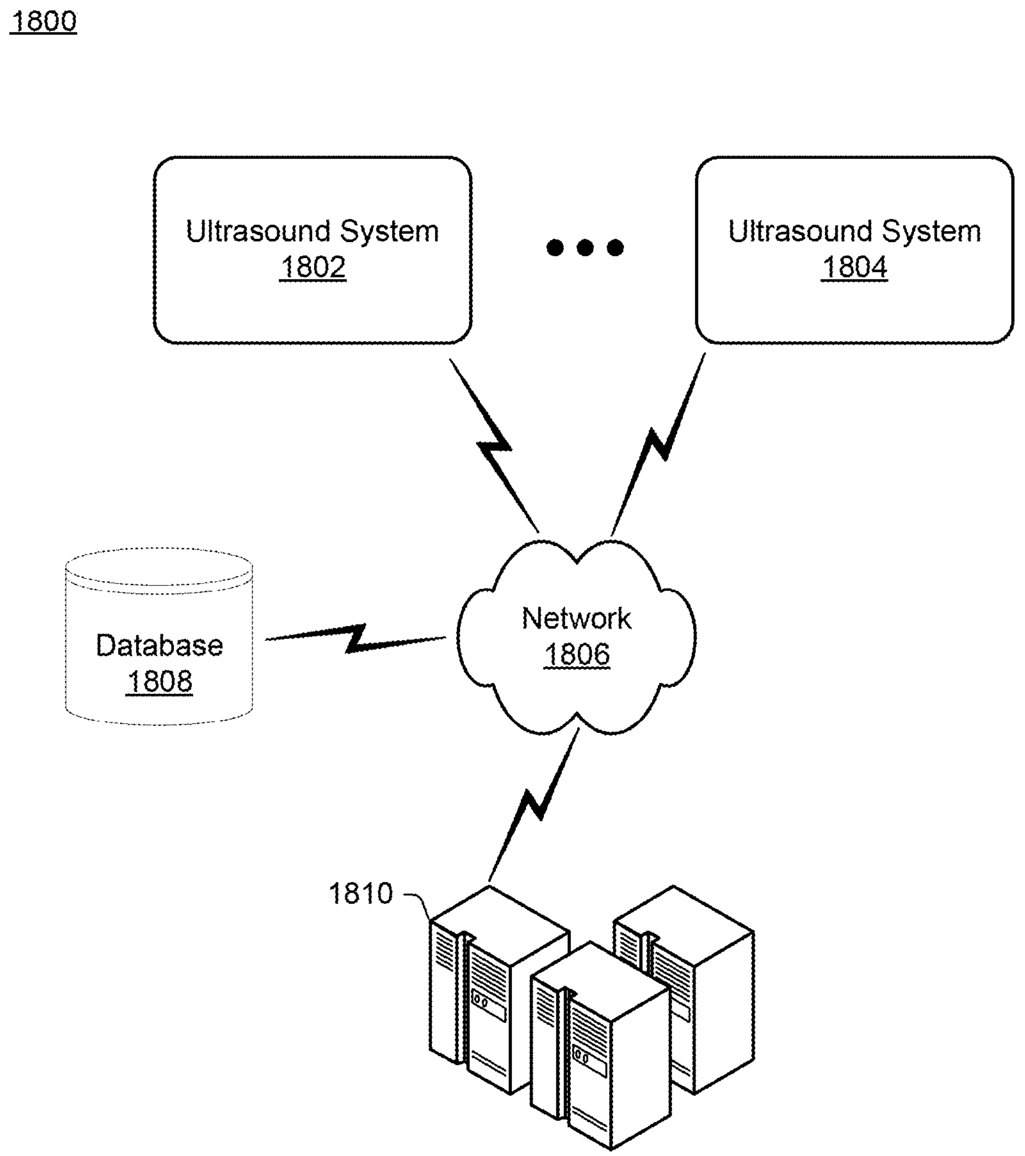
FIG. 18 illustrates an environment for an ultrasound system in accordance with some embodiments.

FIG. 18 illustrates an environment 1800 for an ultrasound system in accordance with some embodiments. The environment 1800 includes an ultrasound system 1802 and an ultrasound system 1804. Two example ultrasound systems 1802 and 1804 are illustrated in FIG. 18 for clarity. However, the environment 1800 can include any suitable number of ultrasound systems, such as the ultrasound systems maintained by a care facility or the department of a care facility. Generally, an ultrasound system can include any suitable device (e.g., a component of an ultrasound system). Examples devices of the ultrasound systems 1802 and 1804 include a charging station, an ultrasound machine, a display device (e.g., a tablet or smartphone), an ultrasound scanner, and an ultrasound cart. Other examples include a transducer cable, a transducer cable holder, a docking station for an ultrasound machine, a scanner station configured to hold one or more ultrasound scanners, a needle guide, a battery for a wireless ultrasound scanner, a battery for an ultrasound machine, a registration system, and the like.

The ultrasound systems 1802 and 1804 can be in communication via the network 1806 as part of the environment 1800. The network 1806 can include any suitable network, such as a local area network, a wide area network, a near field communication network, the Internet, an intranet, an extranet, a system bus that couples devices or device components (e.g., in an ASIC, FPGA, or SOC), and combinations thereof. Accordingly, in embodiments, information can be communicated to the ultrasound systems 1802 and 1804 through the network 1806. For instance, the database 1808 can store instructions executable by a processor system of the ultrasound systems 1802 and 1804, and communicate the instructions via the network 1806. The database 1808 can store parameters (e.g., default parameters) generated as part of the feature enhancement process described herein and share them with the ultrasound systems 1802 and 1804.

In some embodiments, the environment 1800 also includes a server system 1810 that can implement any of the functions described herein. The server system 1810 can be a separate device from the ultrasound systems 1802 and 1804. Alternatively, the server system 1810 can be included in at least one of the ultrasound systems 1802 and 1804. In some embodiments, the server system 1810 and the database 1808 are included in at least one of the ultrasound systems 1802 and 1804. In some embodiments, the server system 1810 is implemented as a remote server system that is remote from (e.g., not collocated with) the ultrasound systems 1802 and 1804. Such remote availability can allow clinicians to access the parameters (e.g., default parameters) generated as part of the feature enhancement process described herein that they created at one location at other locations at which they perform.

There are a number of example embodiments described herein.

Example 1 is an ultrasound system comprising: an ultrasound scanner configured to transmit ultrasound at a patient anatomy and receive reflections of the ultrasound from the patient anatomy; a processor system configured to: generate an ultrasound image based on the reflections and system parameters of the ultrasound system; determine a region of interest (ROI) in the ultrasound image; determine an enhancement property for the ROI; adjust at least one of the system parameters; and generate, based on the at least one of the system parameters being adjusted, a ROI image having the enhancement property enhanced compared to the ROI in the ultrasound image; and a display device configured to simultaneously display the ultrasound image and the ROI image.

Example 2 is the ultrasound system of example 1 that may optionally that the enhancement property is selected from the group consisting of resolution, penetration, contrast, speckle reduction, frame rate, flow resolution, flow density, and color sensitivity.

Example 3 is the ultrasound system of example 1 that may optionally that the processor system is implemented to determine a ROI image property for the ROI in the ultrasound image, and the adjustment of the at least one of the system parameters is based on the ROI image property.

Example 4 is the ultrasound system of example 3 that may optionally that the ROI image property is selected from the group consisting of a spectrum, a signal strength, a noise level, a signal-to-noise ratio, a brightness, a resolution, a clutter, grating lobes, artifacts, a dynamic range, a uniformity, an edge definition, a smoothness, a line connectivity, hole fillings, a flow strength, a flow continuity, and a flow dynamic range.

Example 5 is the ultrasound system of example 1 that may optionally that the at least one of the system parameters includes one or more of a transmit waveform, a transmit voltage, a transmit aperture, an analog gain, a digital gain, an analog-to-digital converter cutoff frequency, a dynamic range, a filter bandwidth, a compression curve, a persistence, a receive aperture, a receive weight, a color map, a color mask, and beam compounding parameters.

Example 6 is the ultrasound system of example 1 that may optionally a memory storage device implemented to store the at least one of the system parameters that have been adjusted as part of a default system configuration for use in a subsequent ultrasound examination, the ultrasound scanner configured to transmit the ultrasound and receive the reflections as part of a current ultrasound examination.

Example 7 is the ultrasound system of example 6 that may optionally that the processor system is implemented to receive a user confirmation of the ROI image, and the memory storage device is implemented to store the at least one of the system parameters responsive to the user confirmation.

Example 8 is the ultrasound system of example 1 that may optionally that the processor system is implemented to obtain an adjustment value for the adjustment of the at least one of the system parameters from a memory storage device as part of a current ultrasound examination, the adjustment value having been determined as part of a previous ultrasound examination.

Example 9 is the ultrasound system of example 1 that may optionally that the determination of the enhancement property for the ROI includes to receive a user selection of the enhancement property.

Example 10 is the ultrasound system of example 1 that may optionally that the processor system is configured to implement a machine-learned model to determine the enhancement property for the ROI.

Example 11 is the ultrasound system of example 1 that may optionally that the determination of the ROI in the ultrasound image includes to receive a user selection of the ROI in the ultrasound image.

Example 12 is the ultrasound system of example 1 that may optionally that the processor system is configured to implement a machine-learned model to determine the ROI in the ultrasound image.

Example 13 is the ultrasound system of example 1 that may optionally that the processor system is implemented to determine an additional enhancement property for the ROI and generate an additional ROI image having the additional enhancement property enhanced compared to the ROI in the ultrasound image, wherein the display device is implemented to simultaneously display the ultrasound image, the ROI image, and the additional ROI image.

Example 14 is the ultrasound system of example 1 that may optionally that the processor system is implemented to: make an additional adjustment to the at least one of the system parameters or another of the system parameters; and generate, based on the additional adjustment, an additional ROI image having the enhancement property enhanced compared to the ROI in the ultrasound image, wherein the display device is implemented to simultaneously display the ultrasound image, the ROI image, and the additional ROI image.

Example 15 is the ultrasound system of example 14 that may optionally that the display device is implemented to receive a user selection that refuses the ROI image, and the processor system is implemented to make the additional adjustment and generate the additional ROI image responsive to the user selection.

Example 16 is an ultrasound system comprising: an ultrasound scanner configured to transmit ultrasound at a patient anatomy and receive reflections of the ultrasound from the patient anatomy as part of a current ultrasound examination; a processor system configured to: generate an ultrasound image based on the reflections and system parameters of the ultrasound system; determine a region of interest (ROI) in the ultrasound image; determine an enhancement property for the ROI; determine, based on the enhancement property, ROI image properties for the ROI in the ultrasound image; determine adjustments to one or more of the system parameters, the adjustments corresponding to the ROI image properties; and generate, based on the adjustments, ROI images having the enhancement property enhanced compared to the ROI in the ultrasound image, the ROI images excluding image content of the ultrasound image that is not contained in the ROI; and a display device configured to simultaneously display the ultrasound image and the ROI images.

Example 17 is the ultrasound system of example 16 that may optionally that the display device is implemented to receive a user selection of one of the ROI images, and the processor system is implemented to cause the adjustments to the one or more of the system parameters that correspond to the one of the ROI images to be stored in a memory storage device for use in a subsequent ultrasound examination.

Example 18 is the ultrasound system of example 16 that may optionally that the enhancement property includes a spatial resolution, the ROI image properties include a lateral resolution and an axial resolution, and the one or more of the system parameters include at least one of an analog gain, a digital gain, and a transmit frequency.

Example 19 is the ultrasound system of example 16 that may optionally that the enhancement property includes a penetration, the ROI image properties include a signal strength and a brightness, and the one or more of the system parameters include at least one of a transmit frequency and a compression curve.

Example 20 is ultrasound system comprising: an ultrasound scanner configured to transmit ultrasound at a patient anatomy and receive reflections of the ultrasound from the patient anatomy as part of a current ultrasound examination; a memory storage device configured to store system parameters, determined as part of a previous ultrasound examination, to enhance an enhancement property in a region of interest (ROI) in a previous ultrasound image generated during the previous ultrasound examination; and a processor system. The processor system is configured to, as part of the current ultrasound examination: generate an ultrasound image based on the reflections; determine a current ROI in the ultrasound image, the current ROI including the patient anatomy; determine that the ROI and the current ROI include the patient anatomy; configure, based on the determination that the ROI and the current ROI include the patient anatomy, the ultrasound system with the system parameters stored in the memory storage device; and generate, based on the ultrasound system configured with the system parameters, a ROI image having the enhancement property enhanced compared to the current ROI in the ultrasound image. The ultrasound system also includes a display device configured to simultaneously display the ultrasound image and the ROI image.

Example 21 is the ultrasound system of example 11 that may optionally that the processor system is implemented to receive a user selection of the enhancement property, and said configure is based on the user selection.

All of the methods and tasks described herein may be performed and fully automated by a computer system. The computer system may, in some cases, include multiple distinct computers or computing devices (e.g., physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (e.g., solid state storage devices, disk drives, etc.). The various functions disclosed herein may be embodied in such program instructions or may be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid-state memory chips or magnetic disks, into a different state. In some embodiments, the computer system may be a cloud-based computing system whose processing resources are shared by multiple distinct business entities or other users.

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in some embodiments, operations or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware (e.g., ASICs or FPGA devices), computer software that runs on computer hardware, or combinations of both. Moreover, the various illustrative logical blocks and modules described in connection with the embodiments disclosed herein can be implemented or performed by a machine, such as a processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the rendering techniques described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without other input or prompting, whether these features, elements or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, or Z). Thus, such disjunctive language is not generally intended to, and should not, imply that certain embodiments require at least one of X, at least one of Y, and at least one of Z to each be present.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

We claim:

1. An ultrasound system comprising:

an ultrasound scanner configured to transmit ultrasound at a patient anatomy and receive reflections of the ultrasound from the patient anatomy;

a processor system configured to, as part of an ultrasound scanning workflow:

generate an ultrasound image based on the reflections and system parameters of the ultrasound system;

determine a region of interest (ROI) in the ultrasound image;

determine an enhancement property for the ROI;

adjust at least one of the system parameters that controls ultrasound signal transmission or reception for ultrasound scanning; and perform a subsequent ultrasound scanning of ultrasound transmission and reception with the ultrasound scanner using the system parameters to generate, based on the at least one of the system parameters being adjusted, a ROI image having the enhancement property enhanced compared to the ROI in the ultrasound image, wherein image content not contained in the ROI is excluded by limiting at least one of ultrasound transmission, reception, or beamforming to the ROI; and a display device configured to simultaneously display the ultrasound image and the ROI image.

2. The ultrasound system as described in claim 1, wherein the enhancement property is selected from the group consisting of resolution, penetration, contrast, speckle reduction, frame rate, flow resolution, flow density, and color sensitivity.

3. The ultrasound system as described in claim 1, wherein the processor system is implemented to determine a ROI image property for the ROI in the ultrasound image, and the adjustment of the at least one of the system parameters is based on the ROI image property.

4. The ultrasound system as described in claim 3, wherein the ROI image property is selected from the group consisting of a spectrum, a signal strength, a noise level, a signal-to-noise ratio, a brightness, a resolution, a clutter, grating lobes, artifacts, a dynamic range, a uniformity, an edge definition, a smoothness, a line connectivity, hole fillings, a flow strength, a flow continuity, and a flow dynamic range.

5. The ultrasound system as described in claim 1, wherein the at least one of the system parameters includes one or more of a transmit waveform, a transmit voltage, a transmit aperture, an analog gain, a digital gain, an analog-to-digital converter cutoff frequency, a dynamic range, a filter bandwidth, a compression curve, a persistence, a receive aperture, a receive weight, a color map, a color mask, and beam compounding parameters.

6. The ultrasound system as described in claim 1, further comprising a memory storage device implemented to store the at least one of the system parameters that have been adjusted as part of a default system configuration for use in a subsequent ultrasound examination, the ultrasound scanner configured to transmit the ultrasound and receive the reflections as part of a current ultrasound examination.

7. The ultrasound system as described in claim 6, wherein the processor system is implemented to receive a user confirmation of the ROI image, and the memory storage device is implemented to store the at least one of the system parameters responsive to the user confirmation.

8. The ultrasound system as described in claim 1, wherein the processor system is implemented to obtain an adjustment value for the adjustment of the at least one of the system parameters from a memory storage device as part of a current ultrasound examination, the adjustment value having been determined as part of a previous ultrasound examination.

9. The ultrasound system as described in claim 1, wherein the determination of the enhancement property for the ROI includes to receive a user selection of the enhancement property.

10. The ultrasound system as described in claim 1, wherein the processor system is configured to implement a machine-learned model to determine the enhancement property for the ROI.

11. The ultrasound system as described in claim 1, wherein the determination of the ROI in the ultrasound image includes to receive a user selection of the ROI in the ultrasound image.

12. The ultrasound system as described in claim 1, wherein the processor system is configured to implement a machine-learned model to determine the ROI in the ultrasound image.

13. The ultrasound system as described in claim 1, wherein the processor system is implemented to determine an additional enhancement property for the ROI and generate an additional ROI image having the additional enhancement property enhanced compared to the ROI in the ultrasound image, wherein the display device is implemented to simultaneously display the ultrasound image, the ROI image, and the additional ROI image.

14. The ultrasound system as described in claim 1, wherein the processor system is implemented to:

make an additional adjustment to the at least one of the system parameters or another of the system parameters; and generate, based on the additional adjustment, an additional ROI image having the enhancement property enhanced compared to the ROI in the ultrasound image;

wherein the display device is implemented to simultaneously display the ultrasound image, the ROI image, and the additional ROI image.

15. The ultrasound system as described in claim 14, wherein the display device is implemented to receive a user selection that refuses the ROI image, and the processor system is implemented to make the additional adjustment and generate the additional ROI image responsive to the user selection.

16. The ultrasound system as described in claim 1, wherein one or both of the enhancement property and adjustment of system parameters are determined automatically by the processor system.

17. An ultrasound system comprising:

an ultrasound scanner configured to transmit ultrasound at a patient anatomy and receive reflections of the ultrasound from the patient anatomy as part of a current ultrasound examination;

a processor system configured to, as part of an ultrasound scanning workflow:

generate an ultrasound image based on the reflections and system parameters of the ultrasound system;

determine a region of interest (ROI) in the ultrasound image;

determine an enhancement property for the ROI;

determine, based on the enhancement property, ROI image properties for the ROI in the ultrasound image;

determine adjustments to one or more of the system parameters that control ultrasound signal transmission or reception for ultrasound scanning, the adjustments corresponding to the ROI image properties; and perform a subsequent ultrasound scanning of ultrasound transmission and reception to generate, based on the adjustments, ROI images having the enhancement property enhanced compared to the ROI in the ultrasound image, wherein image content not contained in the ROI is excluded by limiting at least one of ultrasound transmission, reception, or beamforming to the ROI; and a display device configured to simultaneously display the ultrasound image and the ROI images.

18. The ultrasound system as described in claim 17, wherein the display device is implemented to receive a user selection of one of the ROI images, and the processor system is implemented to cause the adjustments to the one or more of the system parameters that correspond to the one of the ROI images to be stored in a memory storage device for use in a subsequent ultrasound examination.

19. The ultrasound system as described in claim 17, wherein the enhancement property includes a spatial resolution, the ROI image properties include a lateral resolution and an axial resolution, and the one or more of the system parameters include at least one of an analog gain, a digital gain, and a transmit frequency.

20. The ultrasound system as described in claim 17, wherein the enhancement property includes a penetration, the ROI image properties include a signal strength and a brightness, and the one or more of the system parameters include at least one of a transmit frequency and a compression curve.

21. An ultrasound system comprising:

an ultrasound scanner configured to transmit ultrasound at a patient anatomy and receive reflections of the ultrasound from the patient anatomy as part of a current ultrasound examination;

a memory storage device configured to store system parameters, determined as part of a previous ultrasound examination, that control ultrasound signal transmission or reception to enhance an enhancement property in a region of interest (ROI) in a previous ultrasound image generated during the previous ultrasound examination;

a processor system configured to, as part of the current ultrasound examination:

generate an ultrasound image based on the reflections;

determine a current ROI in the ultrasound image, the current ROI including the patient anatomy;

determine that the ROI and the current ROI include the patient anatomy;

configure, based on the determination that the ROI and the current ROI include the patient anatomy, the ultrasound system for subsequent ultrasound transmission and reception with the system parameters stored in the memory storage device; and perform the ultrasound scanning with the ultrasound scanner using the system parameters to generate, based on the ultrasound system configured with the system parameters, a ROI image having the enhancement property enhanced compared to the current ROI in the ultrasound image, wherein image content not contained in the ROI is excluded by limiting at least one of ultrasound transmission, reception, or beamforming to the ROI; and a display device configured to simultaneously display the ultrasound image and the ROI image.

22. The ultrasound system as described in claim 21, wherein the processor system is implemented to receive a user selection of the enhancement property, and said configure is based on the user selection.

* * * * *